(12) United States Patent
Dehnad et al.

(10) Patent No.: US 10,004,548 B2
(45) Date of Patent: Jun. 26, 2018

(54) BONE IMPLANTS FOR THE TREATMENT OF INFECTION

(71) Applicant: Silver Bullet Therapeutics, Inc., San Jose, CA (US)

(72) Inventors: Houdin Dehnad, El Granada, CA (US); Bohdan Wolodymyr Chopko, Henderson, NV (US); Paul E. Chirico, Campbell, CA (US)

(73) Assignee: Silver Bullet Therapeutics, Inc., San Jose, CA (US)

( * ) Notice: Subject to any disclaimer, the term of this patent is extended or adjusted under 35 U.S.C. 154(b) by 0 days. days.

(21) Appl. No.: 15/012,803

(22) Filed: Feb. 1, 2016

(65) Prior Publication Data

US 2016/0157907 A1 Jun. 9, 2016

Related U.S. Application Data

(63) Continuation of application No. 13/527,389, filed on Jun. 19, 2012, now Pat. No. 9,248,254, which is a
(Continued)

(51) Int. Cl.
| | |
|---|---|
| *A61B 17/04* | (2006.01) |
| *A61B 17/84* | (2006.01) |
| *A61F 2/08* | (2006.01) |
| *A61B 17/86* | (2006.01) |
| *A61M 25/00* | (2006.01) |

(Continued)

(52) U.S. Cl.
CPC ............ *A61B 17/866* (2013.01); *A61B 17/56* (2013.01); *A61L 31/022* (2013.01); *A61L 31/088* (2013.01); *A61L 31/16* (2013.01); *A61M 25/0084* (2013.01); *A61B 2017/00893* (2013.01); *A61B 2017/561* (2013.01); *A61F 2002/30677* (2013.01); *A61F 2310/00113* (2013.01); *A61L 2300/102* (2013.01); *A61L 2300/104* (2013.01); *A61L 2300/404* (2013.01); *A61L 2300/602* (2013.01); *A61L 2400/16* (2013.01)

(58) Field of Classification Search
CPC combination set(s) only.
See application file for complete search history.

(56) References Cited

U.S. PATENT DOCUMENTS

| | | |
|---|---|---|
| 2,998,007 A | 8/1961 | Herzog |
| 3,921,632 A | 11/1975 | Bardani |
| (Continued) | | |

FOREIGN PATENT DOCUMENTS

| | | |
|---|---|---|
| DE | 102006004628 A1 | 8/2007 |
| WO | WO 99/44538 A1 | 9/1999 |
| (Continued) | | |

*Primary Examiner* — Sameh Boles
(74) *Attorney, Agent, or Firm* — Shay Glenn LLP

(57) ABSTRACT

Described herein are devices, systems and methods for treating disease and/or infection by the release of silver from an implant over an extended period of time. In particular, the devices described herein may be used to treat infections such as osteomyelitis by the controlled release of silver ions from multiple sites of an extended-use implant. This implant typically includes a plurality of arms that both anchor and help distribute the released ions within the tissue. Power may be applied to release the silver ions into the tissue.

7 Claims, 29 Drawing Sheets

Related U.S. Application Data continuation of application No. 12/870,082, filed on Aug. 27, 2010, now Pat. No. 8,221,396.

(60) Provisional application No. 61/359,549, filed on Jun. 29, 2010, provisional application No. 61/340,587, filed on Mar. 19, 2010, provisional application No. 61/237,506, filed on Aug. 27, 2009.

(51) Int. Cl.
| | | |
|---|---|---|
| *A61B 17/56* | (2006.01) | |
| *A61L 31/02* | (2006.01) | |
| *A61L 31/08* | (2006.01) | |
| *A61L 31/16* | (2006.01) | |
| *A61B 17/00* | (2006.01) | |
| *A61F 2/30* | (2006.01) | |

(56) References Cited

U.S. PATENT DOCUMENTS

| | | | |
|---|---|---|---|
| 4,292,968 | A | 10/1981 | Ellis |
| 4,314,554 | A | 2/1982 | Greatbatch |
| 4,405,311 | A | 9/1983 | Greatbatch |
| 4,615,705 | A | 10/1986 | Scales et al. |
| 4,772,266 | A | 9/1988 | Groshong |
| 4,849,223 | A | 7/1989 | Pratt et al. |
| 5,290,271 | A | 3/1994 | Jernberg |
| 5,372,599 | A | 12/1994 | Martins |
| 5,383,935 | A | 1/1995 | Shirkhanzadeh |
| 5,423,859 | A | 6/1995 | Koyfman et al. |
| 5,454,886 | A | 10/1995 | Burrell et al. |
| 5,505,735 | A | 4/1996 | Li |
| 5,510,109 | A | 4/1996 | Tomioka et al. |
| 5,549,603 | A | 8/1996 | Feiring |
| 5,681,575 | A | 10/1997 | Burrell et al. |
| 5,695,857 | A | 12/1997 | Burrell et al. |
| 5,714,047 | A | 2/1998 | Pedrazzini |
| 5,725,377 | A | 3/1998 | Lemler et al. |
| 5,770,255 | A | 6/1998 | Burrell et al. |
| 5,788,687 | A | 8/1998 | Batich et al. |
| 5,958,440 | A | 9/1999 | Burrell et al. |
| 5,985,308 | A | 11/1999 | Burrell et al. |
| 6,117,296 | A | 9/2000 | Thomson |
| 6,287,484 | B1 | 9/2001 | Hausslein et al. |
| 6,312,469 | B1 | 11/2001 | Gielen et al. |
| 6,425,887 | B1 * | 7/2002 | McGuckin .......... A61B 17/3417 604/272 |
| 6,447,513 | B1 | 9/2002 | Griggs |
| 6,451,003 | B1 | 9/2002 | Prosl et al. |
| 6,458,092 | B1 | 10/2002 | Gambale et al. |
| 6,458,889 | B1 | 10/2002 | Trollsas et al. |
| 6,478,790 | B2 | 11/2002 | Bardani |
| 6,500,165 | B1 | 12/2002 | Frank |
| 6,522,918 | B1 | 2/2003 | Crisp et al. |
| 6,558,388 | B1 | 5/2003 | Bartsch et al. |
| 6,613,807 | B2 | 9/2003 | Uhrich |
| 6,616,678 | B2 | 9/2003 | Nishtala et al. |
| 6,716,895 | B1 | 4/2004 | Terry |
| 6,719,987 | B2 | 4/2004 | Burrell et al. |
| 6,773,429 | B2 | 8/2004 | Sheppard, Jr. et al. |
| 6,830,747 | B2 | 12/2004 | Lang et al. |
| 6,840,919 | B1 | 1/2005 | Håkansson |
| 6,913,763 | B2 | 7/2005 | Lerner |
| 6,936,006 | B2 | 8/2005 | Sabra |
| 6,936,270 | B2 | 8/2005 | Watson et al. |
| 6,960,215 | B2 | 11/2005 | Olson, Jr. et al. |
| 7,147,865 | B2 | 12/2006 | Fishman et al. |
| 7,179,849 | B2 | 2/2007 | Terry |
| 7,223,227 | B2 | 5/2007 | Pflueger |
| 7,255,713 | B2 | 8/2007 | Malek |
| 7,456,012 | B2 | 11/2008 | Rytten et al. |
| 7,457,667 | B2 | 11/2008 | Skiba |
| 7,632,277 | B2 | 12/2009 | Woll et al. |
| 7,662,176 | B2 | 2/2010 | Skiba et al. |
| 7,672,719 | B2 | 3/2010 | Skiba et al. |
| 7,704,520 | B1 | 4/2010 | Calhoun |
| 7,727,221 | B2 | 6/2010 | Penner et al. |
| 7,824,699 | B2 | 11/2010 | Ralph et al. |
| 7,846,162 | B2 | 12/2010 | Nelson |
| 7,904,147 | B2 | 3/2011 | Schneider et al. |
| 7,919,111 | B2 | 4/2011 | Chudzik et al. |
| 7,951,853 | B2 | 5/2011 | Ismail et al. |
| 7,955,636 | B2 | 6/2011 | Terry |
| 7,985,415 | B2 | 7/2011 | Giroux |
| 8,048,150 | B2 | 11/2011 | Weber et al. |
| 8,052,743 | B2 | 11/2011 | Weber et al. |
| 8,080,055 | B2 | 12/2011 | Atanasoska et al. |
| 8,114,148 | B2 | 2/2012 | Atanasoska et al. |
| 8,118,857 | B2 | 2/2012 | VanCamp et al. |
| 8,178,120 | B2 | 5/2012 | Vandesteeg et al. |
| 8,221,396 | B2 | 7/2012 | Dehnad et al. |
| 8,236,046 | B2 | 8/2012 | Weber |
| 8,267,992 | B2 | 9/2012 | Atanasoska et al. |
| 8,292,932 | B2 | 10/2012 | Matthis et al. |
| 8,309,216 | B2 | 11/2012 | Ohrlander et al. |
| 8,591,531 | B2 | 11/2013 | Buevich et al. |
| 8,636,753 | B2 | 1/2014 | Buevich et al. |
| 8,771,323 | B2 | 7/2014 | Dehnad et al. |
| 8,927,004 | B1 | 1/2015 | Dehnad et al. |
| 8,999,367 | B1 | 4/2015 | Dehnad et al. |
| 9,108,051 | B2 | 8/2015 | Dehnad et al. |
| 9,114,197 | B1 | 8/2015 | Dehnad et al. |
| 9,248,254 | B2 | 2/2016 | Dehnad et al. |
| 2002/0029043 | A1 | 3/2002 | Ahrens et al. |
| 2002/0031601 | A1 | 3/2002 | Darouiche et al. |
| 2002/0082679 | A1 | 6/2002 | Sirhan et al. |
| 2002/0111603 | A1 | 8/2002 | Cheikh |
| 2002/0143302 | A1 | 10/2002 | Hinchliffe et al. |
| 2003/0050689 | A1 * | 3/2003 | Matson ................ A61L 27/306 623/1.15 |
| 2003/0065292 | A1 | 4/2003 | Darouiche et al. |
| 2004/0039441 | A1 | 2/2004 | Rowland et al. |
| 2004/0223944 | A1 | 11/2004 | Capelli |
| 2004/0267234 | A1 | 12/2004 | Heart et al. |
| 2005/0004558 | A1 | 1/2005 | Gambale et al. |
| 2005/0125054 | A1 | 6/2005 | Bhat et al. |
| 2005/0152949 | A1 | 7/2005 | Hotchkiss et al. |
| 2005/0177103 | A1 | 8/2005 | Hunter et al. |
| 2005/0181004 | A1 | 8/2005 | Hunter et al. |
| 2005/0256525 | A1 | 11/2005 | Culbert et al. |
| 2005/0271701 | A1 | 12/2005 | Cottone et al. |
| 2006/0004431 | A1 | 1/2006 | Fuller et al. |
| 2006/0030872 | A1 | 2/2006 | Culbert et al. |
| 2006/0041182 | A1 | 2/2006 | Forbes et al. |
| 2006/0264698 | A1 | 11/2006 | Kondonis et al. |
| 2007/0016163 | A1 | 1/2007 | Santini, Jr. et al. |
| 2007/0141106 | A1 | 6/2007 | Bonutti et al. |
| 2007/0168012 | A1 | 7/2007 | Ragheb et al. |
| 2007/0179609 | A1 | 8/2007 | Goble et al. |
| 2007/0244548 | A1 | 10/2007 | Myers et al. |
| 2007/0260054 | A1 | 11/2007 | Chudzik |
| 2007/0298377 | A1 | 12/2007 | Kenealy et al. |
| 2008/0009888 | A1 | 1/2008 | Ewers et al. |
| 2008/0058733 | A1 | 3/2008 | Vogt et al. |
| 2008/0109034 | A1 | 5/2008 | Mather et al. |
| 2008/0147186 | A1 * | 6/2008 | Joshi .................... A61K 9/0009 623/11.11 |
| 2008/0195033 | A1 | 8/2008 | Eagleson et al. |
| 2008/0195223 | A1 | 8/2008 | Eddin et al. |
| 2008/0255618 | A1 | 10/2008 | Fisher et al. |
| 2008/0319424 | A1 | 12/2008 | Muni et al. |
| 2009/0004239 | A1 | 1/2009 | Ladet et al. |
| 2009/0005867 | A1 | 1/2009 | Lefranc et al. |
| 2009/0005869 | A1 | 1/2009 | Laurencin et al. |
| 2009/0012350 | A1 | 1/2009 | Tihon |
| 2009/0035342 | A1 | 2/2009 | Karandikar et al. |
| 2009/0036744 | A1 | 2/2009 | Vayser |
| 2009/0099613 | A1 | 4/2009 | Vilims |
| 2009/0112236 | A1 | 4/2009 | Stopek |
| 2009/0204129 | A1 | 8/2009 | Fronio |
| 2009/0248048 | A1 | 10/2009 | Milbocker |
| 2010/0076463 | A1 | 3/2010 | Mavani et al. |
| 2010/0092531 | A1 | 4/2010 | Odermatt et al. |

(56) References Cited

U.S. PATENT DOCUMENTS

| | | |
|---|---|---|
| 2010/0131051 A1 | 5/2010 | Peterson |
| 2010/0217370 A1 | 8/2010 | Scheuermann et al. |
| 2010/0249783 A1 | 9/2010 | Triue |
| 2010/0292756 A1 | 11/2010 | Schneider |
| 2010/0326835 A1 | 12/2010 | Speitling |
| 2010/0331966 A1 | 12/2010 | Borck |
| 2011/0091515 A1 | 4/2011 | Zilberman et al. |
| 2011/0125287 A1 | 5/2011 | Hotter et al. |
| 2011/0130774 A1 | 6/2011 | Criscuolo et al. |
| 2011/0153027 A1 | 6/2011 | Behan |
| 2011/0200655 A1 | 8/2011 | Black et al. |
| 2011/0257666 A1 | 10/2011 | Ladet et al. |
| 2012/0148633 A1 | 6/2012 | Sun et al. |
| 2012/0251592 A1 | 10/2012 | Neff et al. |
| 2013/0158571 A1 | 6/2013 | Meneghin et al. |
| 2013/0172915 A1 | 7/2013 | Thomas et al. |
| 2013/0224276 A1 | 8/2013 | Hunter et al. |
| 2013/0245783 A1 | 9/2013 | Thull |
| 2013/0295184 A1 | 11/2013 | Choi et al. |
| 2014/0288607 A1 | 9/2014 | Dehnad et al. |
| 2015/0320989 A1 | 11/2015 | Dehnad et al. |
| 2015/0359946 A1 | 12/2015 | Dehnad et al. |
| 2016/0136335 A1 | 5/2016 | Dehnad et al. |
| 2017/0312399 A1 | 11/2017 | Dehnad et al. |

FOREIGN PATENT DOCUMENTS

| | | |
|---|---|---|
| WO | WO 00/47273 A1 | 8/2000 |
| WO | WO 00/51659 A1 | 9/2000 |
| WO | WO 02/009767 A2 | 2/2002 |
| WO | WO 03/049798 A2 | 6/2003 |
| WO | WO 2004/006885 A2 | 1/2004 |
| WO | WO 2004/026357 A1 | 4/2004 |
| WO | WO 2004/045549 A2 | 6/2004 |
| WO | WO2004/059027 A2 | 7/2004 |
| WO | WO 2005/049105 A2 | 6/2005 |
| WO | WO2005/051448 A1 | 6/2005 |
| WO | WO 2006/135479 A2 | 12/2006 |
| WO | WO 2007/076376 A2 | 7/2007 |
| WO | WO2007/097790 A1 | 8/2007 |
| WO | WO 2007/109069 A2 | 9/2007 |
| WO | WO 2007/117214 A1 | 10/2007 |
| WO | WO2009/158333 A2 | 12/2009 |
| WO | WO2010/111502 A2 | 9/2010 |
| WO | WO 2011/031789 A1 | 3/2011 |
| WO | WO 2011/127149 A1 | 10/2011 |

* cited by examiner

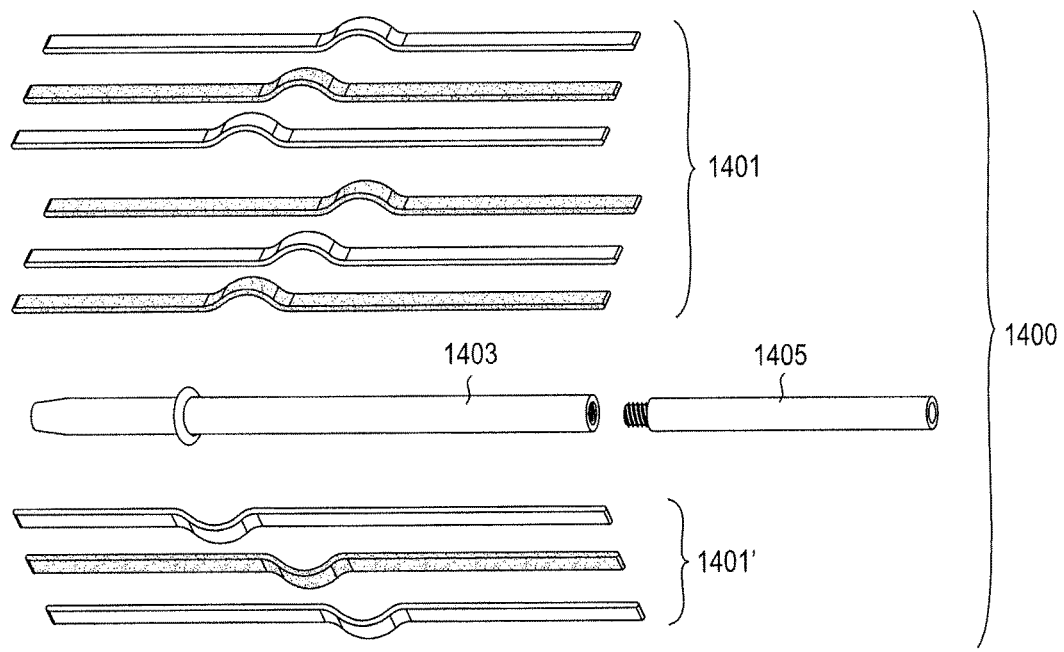
FIG. 14A
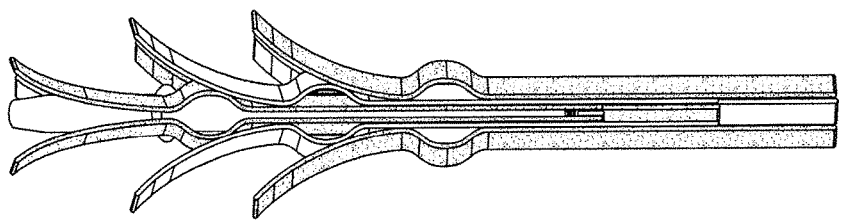
FIG. 14B
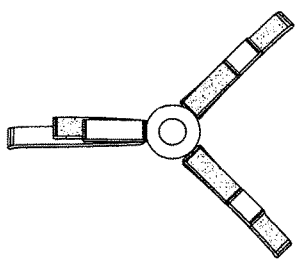 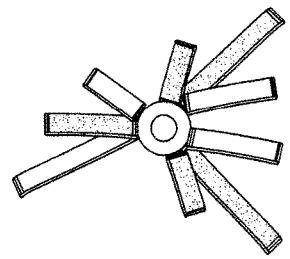
FIG. 14C        FIG. 14D

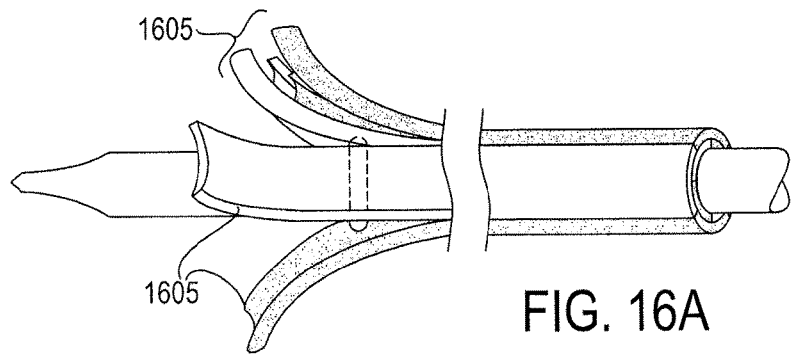
FIG. 16A
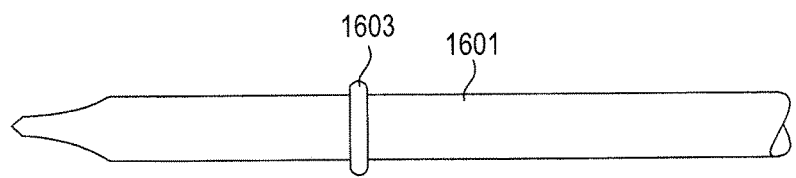
FIG. 16B
FIG. 16C
FIG. 17
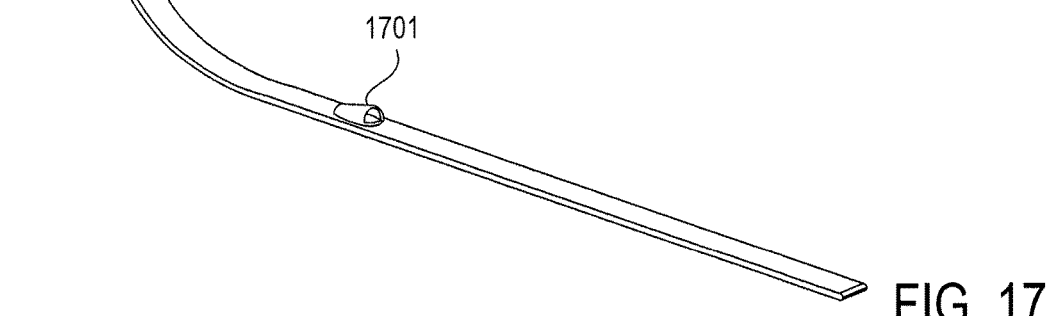
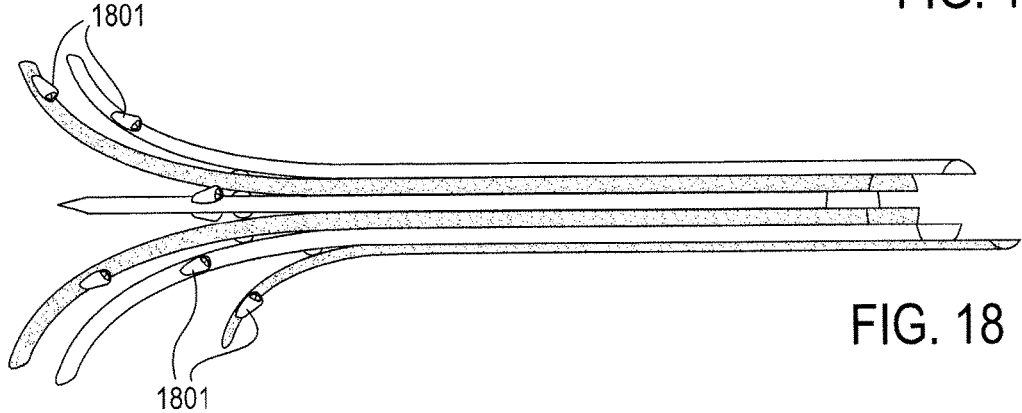
FIG. 18

BONE IMPLANTS FOR THE TREATMENT OF INFECTION

CROSS REFERENCE TO RELATED APPLICATIONS

This patent application is a continuation of U.S. patent application Ser. No. 13/527,389, titled "BONE IMPLANTS FOR THE TREATMENT OF INFECTION," filed Jun. 19, 2012, Publication No. US-2012-0259373-A1, which is a continuation of U.S. patent application Ser. No. 12/870,082, titled "BONE IMPLANTS FOR THE TREATMENT OF INFECTION," filed Aug. 27, 2010, now U.S. Pat. No. 8,221,396, which claims priority to the following U.S. provisional patent applications: Provisional Patent Application No. 61/237,506, titled "SILVER ELLUTING BONE IMPLANTS AND METHODS OF USE," filed on Aug. 27, 2009; Provisional Patent Application No. 61/340,587, titled "ANTIMICROBIAL ION ELUTING IMPLANTABLE DEVICE," filed on Mar. 19, 2010; and Provisional Patent Application No. 61/359,549, titled "SILVER ELUTING BONE IMPLANTS AND METHODS OF USE," filed on Jun. 29, 2010. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, systems and methods described herein relate generally to the treatment of infection, and particularly to the treatment of bone infections such as osetomyelitis using a bone implant that releases silver ions.

BACKGROUND

Bone infections, such as osteomyelitis, can be debilitating or even fatal, and are notoriously difficult to treat. For example, osteomyelitis is an acute or chronic bone infection that may be caused by bacteria or fungi. The infection that causes osteomyelitis may start in another part of the body and spread to the bone through the blood. The infection may also spread to a bone from infected skin, muscles, or tendons next to the bone, as in osteomyelitis that occurs under a chronic skin ulcer (sore). Bone infection can also start after bone surgery, especially if the surgery is done after an injury or if metal rods or plates are placed in the bone. In children, the long bones are usually affected. In adults, the feet, spine bones (vertebrae), and the hips (pelvis) are most commonly affected.

Treatment of osteomyelitis is typically intended to prevent the infection from getting worse and ultimately to eliminate it from the body. The currently accepted treatment for osteomyelitis requires an extended period of intravenous antibiotics. Antibiotics are given to destroy the bacteria causing the infection. More than one antibiotic may be given at a time. The antibiotics are usually given intravenously, and must be taken for at least 4-6 weeks, sometimes longer. In some cases, surgery may be required in order to remove dead bone tissue, and open space left by the removed bone tissue may be filled with bone graft or packing material that promotes the growth of new bone tissue. If an orthopedic prosthesis is present near the site of infection, treatment may also require surgical removal of the prosthesis and infected tissue surrounding the area. A new prosthesis may be implanted in the same operation or delayed until the infection has gone away.

Chronic osteomyelitis may require amputation, especially in patients with diabetes or poor blood circulation. Furthermore, osteomyelitis may be particularly serious when it develops in patients having an implant or prosthesis. When bone becomes infected, pus produced within the bone may result in an abscess that limits the bone's blood supply. The lost blood supply can result in chronic osteomyelitis. This chronic infection can cause symptoms, including pain and disability, which persist for years.

Implants, and particularly silver-coated implants, have been suggested for use to control the spread of bacteria and the development of infection; however, such coatings have not proven effective. Silver coatings have been typically too limited to treat infected regions that are not immediately adjacent to the silver. In addition, the silver in most coatings elutes far too slowly to repel or inhibit colonizing bacteria. Although more quickly-eluting silver coatings have been described, such coatings typically do not last more than a few hours or days, and are not sufficient for the longer-term treatment usually required to treat osteomyelitis and similar infections. In particular, previously described devices are not capable of delivering a sustained level of silver ions to a large region of bone for a sufficient time period.

U.S. Pat. No. 6,500,165 to Frank describes one variation of an active antisepsis device that is intended to actively release silver from an implanted body site. However, this implant is limited by the delivery surface, and is not readily anchorable into a tissue that is already necrotic or damaged by infection, including infected bone tissue. US 2006/00004431 to Fuller et al. describes a similar device, having similar limitations.

Described below are implants that may address these problems and may be used to treat infections such as osteomyelitis. These devices may be implanted over an extended period even in bone or other tissue structures that are damaged or weakened by infection, and release silver ions and/or other antimicrobial or therapeutic substances.

SUMMARY OF THE DISCLOSURE

Described herein are anti-microbial silver-releasing implants that may be used to treat bone infections including osteomyelitis, as well as methods of treating bone infections such as osteomyelitis using these implants.

In general, the devices described herein are implants configured for insertion into a bone for an extended period of time (e.g., days, weeks, months, years, etc.). The bone implant may be anchored within the bone, and typically includes a plurality (e.g., 2 or more, 3 or more, 4 or more, etc.) of arms that are extendable into the bone in a deployed or anchored (or deployed and anchored) configuration. Thus, in general, these implant may have a deployed configuration, in which the arms extend from the implant into the bone along different pathways through the bone, and a delivery configuration, in which the arms are retracted. In the retracted configuration, the implant may be linear or compact, simplifying the insertion into the bone. In some variations, the arms are individually extendable. In some variations the arms are connected to each other and can be extended all together or in subsets.

The arms may be rigid, and may be configured for penetrating the bone, particularly the cancellous bone. For example, the arms may have a sharp or beveled edge. The arms may be formed of a material and/or shape to have sufficient column strength for extending or pushing the arm into the cancellous bone. In other variations, the arms are placed into pre-formed passages, and therefore have only nominal stiffness or rigidity (or column strength). The arms may be elongate members having a tubular or flattened shape. In some variations the arms have a round, oval, rectangular, or other cross-section. In some variations the arms are formed of a metal (including alloys), plastic, ceramic or the like. In particular, the arms may be formed of a shape memory alloy such as a nickel titanium alloy (e.g., Nitinol).

In general, each of the arms in the plurality of arms includes a source of silver. The source of silver may be referred to as a silver reservoir, and may be a solid silver material. The reservoir of silver may be a silver plating or coating on all or a portion of each arm. In some variations, the silver reservoir is a core of silver material within an arm. At least one surface of the reservoir of a particular arm may be exposed along all or portion of the arm. In some variations, different arms include different silver reservoirs and different exposed openings into the reservoirs.

As used herein an arm may include a wire (e.g., filament), a tube, a spike, a coil, etc. An arm is generally elongate and configured for extension from the implant when inserted into the bone (e.g., conversion into the deployed configuration). An arm may be hollow or solid, and may include one or more non-silver-releasing regions as well as silver-releasing regions. In some variations, the arm includes structures that help anchor the arm (or the entire implant) within the bone. For example, the arm may include hooks, notches, prongs, or the like. In some variations the arms include a deflection region that is deflected to extend the arm from the implant when converting the implant into the deployed configuration. The deflection region may be bent, curved, angled, or expanded from the typically more linear configuration of the arm in the delivery configuration. In some variations, the arm is pre-formed into a shape (including the deployed shape), and extending the arm from the implant during deployment into the bone allows the arm(s) to extend to their pre-formed shape. In some variations the arm includes a deflection ramp, notch or other structure to allow another arm to deflect during deployment, by moving against the adjacent arm. Examples of this are described in greater detail below.

The silver reservoir of each arm is typically connected to a silver-release driver that provide motivation to release silver ions from the implant into the bone. The silver-release driver may be a voltage and/or current source, which may in turn be connected to control logic that regulates the power applied (and therefore the silver release). In some variations the silver-release driver is a galvanic reactor metal (e.g., a metal that, when placed in contact with the silver reservoir, drives the galvanic release of silver from the implant).

For example, one variation of an implant as described herein, the implant includes a guide body or structure (including a telescoping body) from which two or more silver-releasing arms (in this example, filaments) may be controllably extended. The implant body and/or the filaments are configured to be inserted into bone in a collapsed configuration in which the arms (filaments) are withdrawn into the guide body. Once inserted within the bone, the filaments may be extended into the bone. The implant may eventually (e.g., after days, weeks, months, etc.) be withdrawn from the bone by withdrawing the filaments back into the guide body (or removing them completely). In some variations, the implant guide body is left in position, and a new "core" region of arms/filaments may be inserted in the same position, using the anchored guide. Thus, the implant may be "recharged" to continue to release silver ions. In this example, one or more power sources may be connected to the silver-releasing electrodes on the filaments and/or the body, so that the silver may be actively released. Also described herein are methods of using these devices and methods and devices for inserting and/or removing them.

As mentioned, some of the implants described herein include a current-controlled or voltage-controlled power source, including control circuitry, connectable to one or more silver-releasing arms (e.g., wires, tubes, spikes, coils, etc.). The devices may be configured to branched delivery of ions (e.g., by including a plurality of ion-delivery elements that branch out to cover an area of tissue and/or bone). In some variations, the device may be galvanic or may include galvanic release of ions in addition to active release. The current used for active release may be in the microamp range (e.g., between about 1 microamp and about 50 microamps, between about 1 to about 30 microamps, between about 1.5 to 15 microamps, etc.).

For example, described herein are implants for insertion in to bone to treat infection, the implant having a collapsed insertion configuration and an expanded deployed configuration. The implant may include: a plurality of arms configured to extend from the implant in the deployed configuration, wherein each of the arms comprises a reservoir of silver configured to be released from the implant into the bone; an elongate and rigid guide comprising a plurality of deflection pathways, wherein the plurality of arms are movably coupled to the elongate guide so that they may be extended from the deflection pathways and deployed to different bone regions to convert the implant from the collapsed insertion configuration into the expanded deployed configuration; and a silver-release driver coupled to the reservoirs of silver to drive release of silver ions from each of the plurality of arms.

In some variations, the implant further includes a bone anchor configured to secure the implant at least partially within a bone. The bone anchor may be coupled to (or integral with) the elongate guide body. For example, the anchor may include one or more fastening or attachment sites for sutures, screws or the like. An anchor may include a projecting element (e.g., prong, etc.) that secured into the bone.

The elongate guide may be an elongate hollow member within which the arms are contained so that they can be extended for deployment. In some variations, the guide is a solid member to which the arms are secured. For example, the guide may include a core member around which the arms are slideably arranged. The guide may include channels, ramps, deflection regions, or the like for guiding each or the arms during deployment (or retrieval). During deployment the distal ends of the arms typically move from the central axis of the implant into an expanded configuration out of the implant.

The deflection pathways of the elongate guide may include openings, e.g., windows, along the long axis of the elongate hollow member. Arms may exit these windows to expand into the bone during deployment.

For example, an elongate guide may include an elongate inner member having a longitudinal axis and a deflection ramp region forming the plurality of deflection pathways that are configured to deflect the arms from longitudinal axis as they are extended into the deployed configuration.

As mentioned above, the plurality of arms may be formed of any appropriate material, including a shape-memory material. For example, in some variations, the arms may comprise a nickel titanium alloy (e.g., Nitinol) covered by a non-reactive (e.g., passivation) layer beneath a silver coating, wherein the non-reactive layer is formed directly onto the nickel titanium material, after removal (or before formation) of a titanium oxide layer from the outer surface of the nickel titanium alloy. The non-reactive layer may be an adhesion layer that enhances the adhesion of silver to the shape-memory material. Typically nickel titanium will form an oxide layer on the outer surface. However, this oxide layer may prevent the material from easily bonding to the silver coating or silver reservoir. Thus a non-reactive layer (e.g., gold, etc.) may be used to both help adhere the silver to the nickel titanium, and to prevent leeching of nickel from the alloy.

The arms may be bent and/or curved when extended in the deployed configuration. As mentioned, the arms may comprise tissue-penetrating ends. In general, the arms are configured to expand within cancellous bone during insertion of the implant. In some variations, the plurality of arms are distributed asymmetrically about the radius of the elongate guide in the insertion configuration.

The plurality of arms may include arms of different lengths, and shapes. The silver reservoirs may be differently positioned and configured on each arm or groups of arms. Typically, the implants described herein may have the arms arranged so that, when the arms are in the expanded configuration, they form a space-filling structure from which silver may be released to cover a predetermined bone region. Thus, the arms may be expanded into different directions and orientations. The arms may be arranged symmetrically or asymmetrically when expanded into the deployed configuration.

The plurality of arms may be configured to release silver along their entire expanded length, or from a plurality of discrete locations along their length. As mentioned, the reservoir of silver may be a silver coating, and/or a silver core.

Also described herein are delivery devices for use with the implants described herein. A delivery device may be adapted to allow insertion and expansion of the implant while in the bone. In some variations the delivery devices may also be configured to allow removal/retrieval of the implant. The delivery device may be used to remove the entire implant or just a portion of the implant, such as the arms, for example, when reloading or recharging the implant with new silver-releasing arms. In some variations the delivery device may be used to remove and replace the silver-release driver or a component of the driver (e.g. battery).

For example, in some variations the implant includes a delivery device coupling region at a proximal end of the elongate guide, wherein the coupling region is configured to couple the implant to a delivery device so that the plurality of arms may be expanded or retracted relative to the elongate guide. The coupling region may be a threaded region, for example. Any appropriate coupling regions may be used. The implant may include a first delivery device coupling region at a proximal end of the elongate guide and a second delivery device coupling region coupled to a proximal end of the plurality of arms, wherein the first delivery device coupling region and the second delivery device coupling region are each configured to couple the implant to a delivery device so that the plurality of arms may be expanded or retracted relative to the elongate guide.

As mentioned, above, the silver-release driver may comprise a battery. In some variations the silver-release driver comprises logic configured to provide pulsatile stimulation to drive release of the silver ions.

Also described herein are implants for insertion into a bone to treat infection, the implant having an expanded deployed configuration configured for long-term release of silver ions and a collapsed insertion configuration. The implant may comprise: an elongate outer housing having a plurality of channel windows along the length of the elongate body; an inner treatment member comprising a plurality of radially-expandable arms configured to extend from the channel windows of the elongate outer body; wherein each of the radially-expandable arms comprises a silver reservoir, and wherein the inner treatment member is axially slideable relative to the outer housing to expand the plurality of radially-expandable arms from the collapsed to the deployed configuration; and a silver-release driver coupled to the reservoirs of silver to drive release of silver ions from each of the plurality of arms.

As mentioned, in some variations the plurality of radially-expandable arms are coated with silver. The plurality of radially-expandable arms may be formed of a material having sufficient stiffness to allow the arms to penetrate the target bone region when extended from the channel windows.

The inner treatment member (or a portion of it) may be formed of a nickel titanium alloy. In some variations, the distal tips of the arms comprise chisel-shaped tissue-penetrating distal tips.

The implant may also include a first applicator coupling region on a proximal end of the outer housing and a second applicator coupling region on the proximal end of the inner treatment member, wherein the coupling regions are configured to couple the implant to a delivery device so that the plurality of arms of the inner treatment member may be expanded or retracted relative to the outer housing.

Also described herein are implants for insertion into a bone to treat infection, the implant having an expanded deployed configuration configured for long-term release of silver ions. The implant may include: a plurality of deflection arms having a first axially elongated delivery configuration and a second radially deflected delivery configuration, wherein each of the deflection arms comprises a silver reservoir, and wherein the deflection arms are further configured to slide axially relative to the other deflection arms to convert the deflection arm from the delivery configuration into the delivery configuration; further wherein the plurality o deflection arms are adjacent to each other; a deflection ramp on each deflection arm configured to convert an adjacent deflection arm from the delivery configuration to the deployed configuration as the adjacent deflection arm is moved axially against the deflection ramp; and a silver-release driver coupled to the reservoirs of silver to drive release of silver ions from each of the plurality of deflection arms.

Also described herein are systems for treating osteomyelitis by inserting an implant configured for the long-term release of silver ions over a region of bone. A system may include a silver-releasing implant (including any of the implants described herein) and a delivery device. For example, the system may include a silver-releasing implant including: a silver-releasing implant having a collapsed insertion configuration and an expanded deployed configuration, the implant comprising: a plurality of arms configured to extend from the implant, wherein each of the arms comprises a reservoir of silver configured to be released from the implant into the bone; an elongate guide forming a plurality of deflection pathways for the arms, wherein the plurality of arms are movably coupled to the elongate guide so that the arms may be extended from the elongate guide at different locations and orientations when the implant is converted to the deployed configuration; a first coupling member on a proximal end of the elongate guide configured for releasably coupling to a delivery device; and a silver-release driver coupled to the reservoirs of silver to drive release of silver ions from each of the arms.

A delivery device may include an elongate insertion member having a distal coupling region configured to releasably couple with the first coupling member; and an arm-extender member configured to couple with and extend the arms of the implant; and a handle at a proximal end of the delivery device.

In some variations, the system includes a control on the distal end configured to control extension/retraction of the arms of the implant. The arm-extender of the delivery device may include a coupling region at the distal end configured to releasably couple with a coupler on the plurality of arms. The arm-extender may be a push rod. In some variations, the arm-extender is slideably disposed within the elongate insertion member for extending or retracting the arms. The arm-extender may be configured to separately engage one or a subset of the plurality of arms and to separately control extension or retraction of the one or a subset of arms.

Also describe herein are methods of treating infection in a bone, the method comprising: inserting a silver-releasing implant into a bone in a collapsed configuration; expanding a plurality of arms from the implant into the bone from the collapsed configuration into an expanded configuration wherein the expanded arms extend in a pattern having multiple pathways through the bone; releasing silver ions from one or more silver reservoirs on the arms into the bone over an extended period of time at a sustained level; and removing the implant after a predetermined period of time that is longer than a week.

The step of inserting may comprise forming passageways (passages) for the implant and the expanded arms (e.g., before insertion of the implant). A device for forming the passageways may be used. This device may be referred to as an implant template or as a passage forming implant or device. The implant template may have an expanded configuration shape that is similar to that of the implant. For example, the implant template device may have a plurality of projecting "arms" that are configured to be inserted into the bone and form passages for the insertion of the implant. In some variations the implant template and/or the arms of the implant template are configured to cut, compress, carve, ablated, or otherwise form channels in the bone into which the implant and the implant arms of the implant can be inserted. For example, the template device may include arms that are rigid, hard, sharp, stiff, or otherwise tissue-penetrating. The arms of the template device may be extendable or expandable. In some variations, the template device is anchored to the bone so that one or more components can be driven into or through the bone to form the arm passageways. A central passageway may be formed first by drilling or other means, and a passageway forming device can then be inserted into the central passageway to form the passages for the arms of the treatment implant. For example, the step of inserting may comprise inserting a passage forming implant having a plurality of expandable members to pre-form the passageways. Thereafter an implant having a plurality of silver-releasing arms may be inserted into the pre-formed passageways. The pre-formed passageways may be large enough to accommodate the treatment implant, or they may act as "pilot" holes or guides through the bone, so that the implant arms themselves still penetrate the tissue, ensuring a tight apposition between the implant and the bone. In some variations the treatment implant has arms that are of relatively low column strength, and benefit from the use of pre-formed passageways.

In some variations, the method includes the step of driving the arms of the implant through the bone by extending the arms from the implant, wherein the arms are sufficiently stiff and/or sharp to penetrate bone.

The method may also include the step of anchoring the implant in the bone. The implant may be anchored before extension/expansion of the arms, or it may be anchored after extension of the arms. Extending the arms into the delivery configuration may help to anchor the implant in position. In some variations the implant includes a guide or reference region, such as a core region or an elongate outer housing, against which the implant arms move to expand into the deployed configuration; this guide or reference region may be anchored, and may include anchors coupled thereto, as mentioned above.

The step of releasing silver ions may comprise applying energy to drive the release of ions. For example, the method may include applying less than 50 microAmps of power to release ions. The step of releasing silver ions may comprise applying pulsatile energy to release ions. The step of releasing silver ions may comprise applying pulses of energy to maintain the silver ion concentration above a minimum inhibitory concentration.

In general, the step of releasing silver ions may include releasing silver ions to maintain the silver ion concentration above a minimum inhibitor concentration in a predetermined region of bone surrounding the implant for a predetermined period of time. The minimum inhibitor concentration is typically the concentration of silver ions necessary to treat infection by killing microorganisms and inhibiting microbial growth. For example, the minimum inhibitory concentration may be between about 0.01 microgram/ml and about 10 microgram/ml (e.g., between 0.1 microgram/ml and about 1 microgram/ml). Any appropriate predetermined time period may be selected, including, for example, about 1 week, 1 month, 2 months, 3 months, 6 months, 1 year, 2 years, etc. (including any time period between 1 week and five years). The implant may be configured to provide the minimum concentration for the predetermined time period based on the power requirements and the silver-release driver (e.g., battery). The region of the bone surrounding the implant is typically a region extending from about a few mm to many cm around the arms of the implant. The arms of the implant may be configured so that the effective range of silver ion elevation to the minimum effective concentration from the various arms overlaps, are adjacent, or are additive in the overlapping regions between adjacent arms. Thus, the implants described herein having multiple arms may provide an enlarged region of elevated silver (compared to implants that do not have multiple arms) even at lower power requirements.

As mentioned, the arms of the implant may be extended by extending them from a guide region and/or by moving the arms relatively to each other (e.g., over or against each other). A delivery device may be used to facilitate the expansion of the arms into the bone. In some variations, the step of inserting comprises inserting the implant with a delivery device configured to hold one region of the implant while longitudinally moving another region of the implant to extend the arms.

After insertion, the silver-releasing (treatment) implant may be removed using an inserter. For example, the implant may be removed with a delivery device configured to secure a proximal region of the implant while longitudinally moving another region of the implant to contract the arms. All or just a portion of the implant may be removed. For example, the arms of the implant may be removed so as to insert a fresh silver reservoir for release. The new implant arms may be inserted into the spaces in the one left by the previous arms, or into new bone regions. In some variations, the silver-release drive may be replaced in this manner, leaving the rest of the implant in position. Alternatively, the arms may be left in position and the rest of the implant (e.g., any core or guide region) may be removed or replaced. In some variations, the entire implant may be removed or replaced.

BRIEF DESCRIPTION OF THE DRAWINGS

FIG. 10C illustrates the implant inserted into a rabbit femur.

FIGS. 14A-14D illustrate another variation of a system including a silver-releasing implant for insertion into a bone to treat infection.

FIGS. 16A-16C show another variation of a silver-releasing implant for insertion into a bone to treat infection.

FIG. 17 shows one variation of an arm including a pair of bone-sampling regions.

FIG. 18 shows one variation of an implant including bone-sampling regions.

DETAILED DESCRIPTION

Figure 1A:
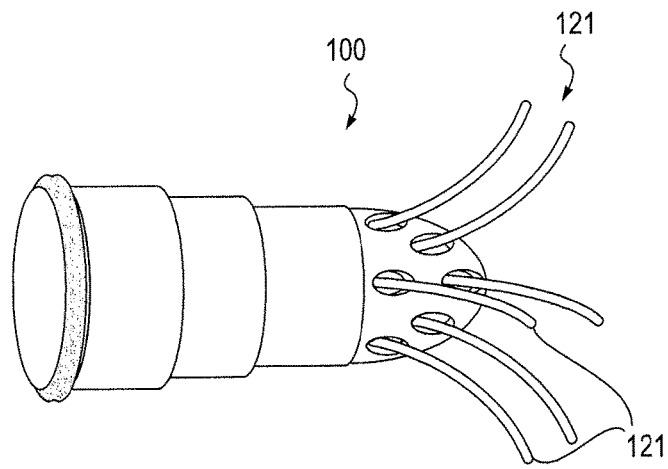
FIG. 1A is one variation of an anti-microbial silver-releasing implant, as described herein.

Described herein are devices, systems and methods for treating bone infection by the active release of an antimicrobial (e.g., silver ions) from an implant. In particular, the devices described herein may be used to infections such as osteomyelitis by the controlled release of silver ions from multiple sites of an extended-use implant. The implant is typically configured to be implanted into bone for an extended period of time (e.g., days, weeks, months, or even longer) and to release silver ions (and in some embodiments other medicaments). In these variations, active release of silver ions may lead to greater tissue concentrations, and thereby have an enhanced bactericidal or therapeutic effect compared to passive (e.g., diffusion) of ions or medicaments.

In some variations of the devices described herein, the implant includes an implantable body from which one or more (often a plurality) of silver-releasing arms (e.g., filaments, plates, wires, branches, etc.) may be extended into the tissue. In particular, the implant may include a guide body having a plurality of silver-releasing arms. The arms are typically extendable from the guide body. The guide body may steer or direct the arms as they are extended from the body, and/or may coordinate the expansion of the arms. The guide body may be an outer member (e.g., a hollow cannula member) out of which the arms extend, or it may be an inner core member against which the arms slide, or some combination thereof. The guide body may include a plurality of channels, openings, deflection ramps, or other guide elements for engaging and guiding the arms. The arms typically slide against (relative to) the guide body. The guide body may be rigid. The guide body is typically elongate (e.g., having a longer length than width) and may have any appropriate cross-section, e.g., round, oval, flat, square, etc.

The arms may be configured to penetrate the bone upon leaving the guide body. For example, the arms maybe reinforced with a durable metal substrate such as a shape memory alloy (e.g., nickel titanium). These arms may be coated, filled, embedded or may otherwise carry a source of silver ions that is in communication with one or more silver-release drivers. In some variations, the silver reservoirs coupled to the silver-release driver by one or more electrical contacts (e.g., an anode (+)); the implant guide body may also includes one or more return contacts (e.g., cathodes (−)) which may be located anywhere on the implant, spaced apart from the cathode, so that silver ions may be released from the implant into the bone or other surrounding tissue. For example, the return contact(s) may be on a different portion of the filament, on another filament, or on the body of the implant.

The body of the device may be configured to penetrate the bone, and may have a tapered distal end and/or tip. In some variations, the distal end of the implant includes bone-engaging members (e.g., teeth, grips, threads, etc.) for securing the implant into the bone; in other variations the distal end of the implant is substantially smooth so that the implant is engaged within the bone by the filaments.

As mentioned, the arms may be extendable and/or retractable from the body of the implant. In some variations, one or more ports, windows, or openings on the guide body region may permit extension of the filaments from the device. The arms maybe extended by advancing out of the body. Thus, the implant may include a delivery configuration in which the one or more arms are retracted within the guide body, and an implanted configuration in which the one or more arms are extended from the body (e.g., out of a port or ports on the body). In some configurations the arms are partially retracted into the body in the delivery configuration, or be flush with the surface of the body. In some variations the arms are retractable back within the body of the implant (e.g., for removal or repositioning of the device). In some variations the arms may be extended gradually or incrementally. For example, as the implant is operated and silver is released from one or more regions of the arms, additional arms (or completely new arms) may be extended from the guide body with additional sources of silver.

Any appropriate arm that may contain or support a source of silver ions for active release may be used. For example, arms may be solid or hollow. Further, the source of silver ions may be applied to the outside of all or a portion of the arm (e.g., by a coating), or it may be contained within the wall of the filament, or within a core region of the arm. In some variations, the arm is filled with the releasable silver. Hollow arms may be particularly useful for co-delivery of other agents such as medicaments in addition to the delivery of silver ions (e.g., antibiotics, bone growth promoting agents, etc.). Thus, the arms may include a lumen or passageway through which material may be released.

The arms may be configured to penetrate tissue, and in particular, they may be configured to penetrate bone. For example, the arms may be reinforced, or may include a relatively stiff material such a metal having a sufficient strength and durability. The distal end of the arm may be tissue penetrating (e.g., sharp). The arm may be any appropriate size. For example an arm may have a diameter of between about 0.05 mm and about 5 mm. The diameter of the arm may be constant, or it may vary along the length of the filament (e.g., it may taper distally). An implant may have arms of different configurations (including lengths, shapes, materials, silver reservoirs, etc.).

Arms may be pre-based to assume a shape when extended from the body of the device. For example, when arms are formed of nickel titanium or other shape-memory materials, the arm may be configured to extend away from the body of the device. The exit port for the arm from the body of the device may include a deflecting surface to direct the arm in a desired location away from the body as it is extended. In variations having more than one arm extendable from the body, the arms may be extended independently or as a group or plurality of groups.

Any of the devices described herein may also include one or more sensors. For example, a pH sensor may be associated with the body of the device for sensing pH in the surrounding of the bone. pH may be one indicator of bacterial load, and the power or frequency of silver release may be modified based on the pH reading. Other sensor may include silver sensors (which may be used to regulate the release). Internal sensors may also be provided. For example, a sensor or detector may be included to monitor or otherwise indicate the level of power in the implant, and/or the level of silver. Information from these sensor(s) may be used by a controller to modify the activity of the device (e.g., increasing/decreasing the release of silver), and/or it may be communicated outside of the patient's body, via a wired or wireless connection.

The active silver-release devices described herein may include an on-board power source (e.g., a battery, inductive coil, etc.) for applying current to release the silver. When a battery is used, the silver source in placed in electrical contact with the battery and the return electrode (e.g., cathode) is also placed in electrical contact with the battery. As mentioned the silver source (and anode) may be present on the arms and the return electrode (cathode) may be present in one or more locations on the body, arm(s) or elsewhere on the device, so that the silver can be released in a desired pattern from the implant when in a subject's body (e.g., within the bone). As mentioned, the device may also include a control or controls (e.g., circuitry) for controlling the applied power (e.g., current and/or voltage), for timing the active powering of the device, and/or for controlling, communication or monitoring with any sensors on the device, or any telemetry associated with the device.

In operation, the device may be controlled so that silver is released continuously or intermittently (in pulses), or based on some pre-determined schedule (e.g., initially higher, or for a longer period, which gradually tapers off). For example, if power is applied by a current or voltage source, power may be applied continuously or in pulses or bursts of pulses. Alternatively, the device may be actively controlled, as mentioned above, so that power is applied based on feedback from the tissue or implant. In some variations, the device applies power to release silver intermittently, for some on-period, followed by a quiescent period (off-time). During the application of power (e.g., current), the power applied may be continuous or variable.

The power may be pulsed (e.g., at some frequency) to help with release of the ions. The current may be applied at any appropriate level. For example, the applied current may be less than 10 mA (e.g., less than 1.0 mA, less than 0.5 mA, etc.). The applied current may depend upon the apparent load of the device (e.g., depending on where in the body—or in the bone—the implant is positioned).

The power source for an implant may be voltage-regulated or current regulated, which may also be referred to as voltage controlled or current controlled. For example, the system may be configured to maintain a target current or a target voltage. A current controlled or voltage controlled system may be used to achieve a constant current/voltage, or when the voltage or current is controlled to be varying (e.g., ramped, pulsed, etc.). The constant current may put out (cause the release of) the same amount of silver, and may adjust the voltage to maintain the target (e.g., constant or relatively constant) current. The device may be limited to prevent excessive voltages. The current controlled embodiments may drive the ion-releasing reaction at a known or predetermined rate. In voltage controlled embodiments, the device may keep the concentration of the silver relatively constant, regardless of the rate of release. This variation may allow the current to vary to achieve a target (e.g., constant) voltage.

In general, the current range for a constant-current configuration may be in the sub-microamp (e.g., nanoamp), microamp, or milliamp range (e.g., approximately 1.5 µA to 15 µA). Although the device may apply current in the milliamps range, this may be unnecessary in order to provide sufficient concentration of ions to have the desired effect. For example, a high-current embodiment may result in an unnecessarily high concentration. In some variations, the applied current is an extremely low current (e.g., in the order of microamps or nanoamps). For example, the current may be between about 1 microamp and 50 microamps. For example, the current applied by the device (constant or varying) may be approximately 1 microamp, 1.5 microamps, 2 microamps, 3 microamps, 4 microamps, 5 microamps, 10 microamps, 15 microamps, 20 microamps, 30 microamps, 40 microamps, 50 microamps, or any value between these).

In some variations the implant is inserted using a telescoping delivery device (e.g., cannula), or the body of the implant is itself telescoping. Telescoping implants may be configured to maximize or increase the tissue/therapeutic interface. In addition, the telescoping implants allow for serial dilation through necrosed or infected bone to healthy bone providing a more stable implant anchor that is fully removable upon therapy completion.

Release of Ions:

As described herein the method of release of silver (or any other ion, particularly antimicrobial ions) may be through an electroporation-like release. A source of silver ions (e.g., silver, silver-ion doped materials, etc.) may be placed in electrical communication with a first electrode (e.g., an anode (+)). A single arm may have one or more such electrodes and/or sources of silver ions. A return electrode (or plurality of return electrodes (e.g., cathode (−)) may be placed some distance from the first electrode(s), so that when power is applied across these first electrode(s) and the return electrodes, ions are released to travel into the body by the flow of current.

The arm structures described herein may be expanding structures that both penetrate and anchor the implant into the tissue, and also establish a broad distribution pattern for the ion distribution. These arms (which may be a stiff, non-eroding material such as Nitinol) may stabilize the implant even in necrotic bone or other tissues and be fully retractable upon completion of therapy.

Although many of the variations described herein are powered by on-board power sources (e.g., battery, induction coil, etc.), they may also be powered by an off-board power source, and may include a cable or wire connection. For example, in some variations, the devices may be placed or positioned by guidewire. The guidewire may also be used to provide power to the device (thus the guidewire may be otherwise insulated).

In any of the variations described herein the device may include one or more on-board controllers, and may be controlled automatically, programmed, or may receive input from one or more sensors or communication sources (e.g., wireless communication) that may control one or more aspects of the device (including the time on/time off/frequency of current applied/level of current applied/voltage applied/etc.). The power source may be internalized (within the implant), and could use external control (e.g., an external magnetic field) to activate/deactivate. In some variations, communication or control may be via RF communication.

Thus, in any of these variations, the device may be anchored into the bone, at or near an infection site, or prophylactically near a site that is prone for infection (e.g., near another implant or orthopedic device). The implant may be configured to expand upon insertion so that the arms are separated from the return electrode(s) in a pattern sufficient to apply silver ions to the infection region at the desired effective level.

In some variations the creation and release of the ions (e.g., silver ions) may be galvanic or may be galvanic in addition to the active (powered) techniques described above. For example, germicidal ions may be generated by coupling a metal with antimicrobial ions properties (such as silver or zinc) with another metal to form a galvanic cell. For example, a silver wire, plating, or film (either mechanical deposited or chemical deposited) or a material having silver as a component of an alloy, may be placed in contact with another metal or alloy in form of a wire, plating, film or a component of an alloy, to create a galvanic cell that creates and releases germicidal ions such as Pt, Pd, Au, etc. In one variation, the device includes one or more Nitinol supports (e.g., wires) having a silver coating connected to a conductive component (stainless steel or Nitinol) with Pt, Pd or gold coating.

Figure 11A:
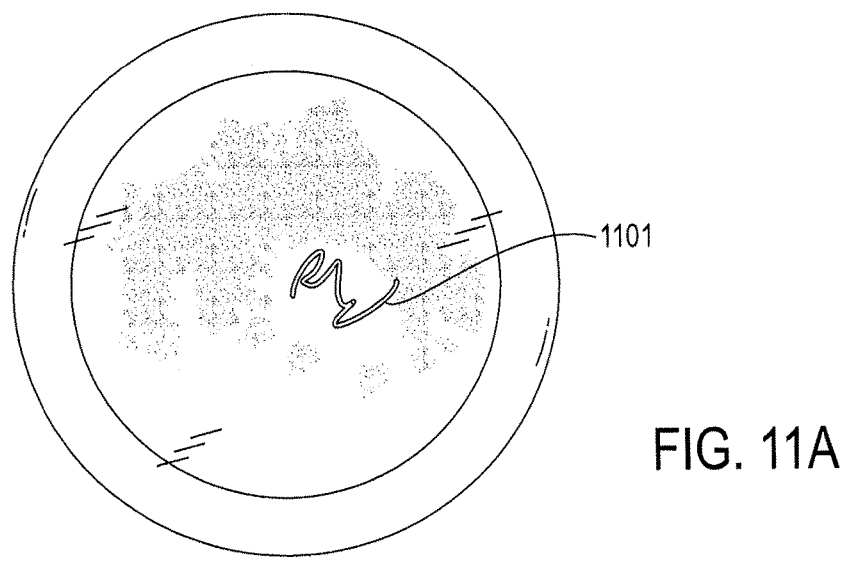
FIG. 11A illustrates the effect of an implant that uses galvanic release of ions.

FIG. 11A illustrates the efficacy of galvanically generated silver ions in preventing bacterial growth (1101 clear zones in the figure). In this example, silver wire has been wrapped with another metal (e.g., Pt) to create a galvanic response that causes the release of silver ions. The released silver ion results demonstrated that bacteria were killed and bacterial growth inhibited in a cleared area around the growing bacterial colonies.

Figure 11B:
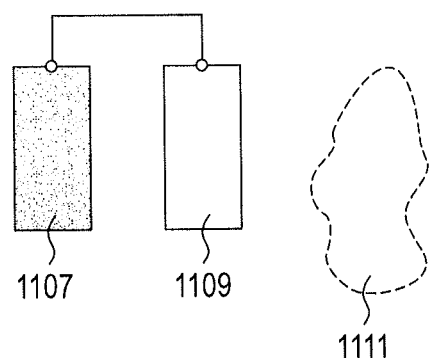
FIGS. 11B and 11C illustrate one variation of the galvanic release of silver ions which may be used in an implant as described herein.
Figure 11C:
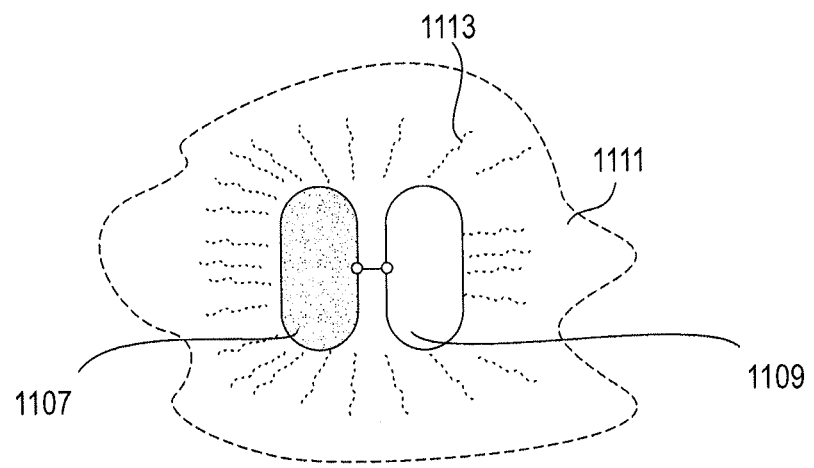

FIG. 11B shows a schematic of the galvanic action resulting in silver release. In this example, the silver material 1107 (e.g., a reservoir of silver on an arm) is placed in electrical contact with a galvanic reactor metal 1109. The two materials may be surrounded by the cancellous bone and any ionic and/or conductive material (e.g., saline, blood, cellular matrix, etc.) therein. In general, the galvanic reactor metal 1109 in this example is typically a more noble metal or alloy than silver (e.g., platinum). This contact (in the conductive medium) may result in an oxidation-reduction reaction, leading to the release of silver ions by the galvanic reaction. This is shown in FIG. 11C, resulting in a region surrounding the metals (within the bone, for example) of increased silver ions by the release 1111. The released silver 1113 may diffuse or be actively driven from the cathode (silver 1107) into the surrounding bone.

In some variations the galvanic activity/release is aided or assisted by active (electrical) source.

Any of the treatment devices described herein may also be retrievable. For example, the extended arms may be retracted to remove the device. In some variations, the body of the device is telescoping, so that it can be collapsed into the bone both to distract the bone region, and also to allow the device to be wholly inserted into the body and/or bone. The telescoping body may be extended to retract the device.

The implant may be inserted quickly, but may remain in the body for an extended period (e.g., weeks, months, years). For example, the implant may remain implanted in a bone for a month. In addition, the core of the implant or cartridge may be removed from the outer telescoping body that is left within the bone and replaced as a recharge or refreshed therapeutic unit.

The implants may be any appropriate size. For example, an implant appropriate for spine may be smaller than the size of a vertebral body (e.g., between 8-50 mm in diameter)

Figure 1B:
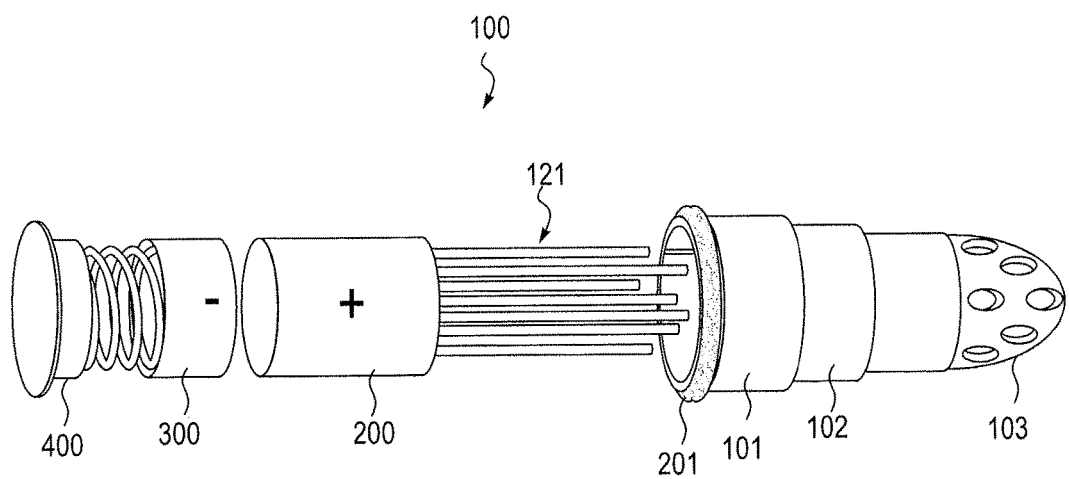
FIG. 1B is an exploded view of the implant of FIG. 1A.

FIGS. 1A and 1B illustrate one variation of a silver-releasing implant as described herein. FIG. 1B provides an exploded view of the implant of FIG. 1A. In this example, the implant 100 is configured as a telescoping implant. The body of the implant 100 is shown in the figures. The arms 121 (which may also be referred to as filaments or fibers) are shown extended in FIG. 1A. In some variations the devices may include additional anchoring or securing features or members. For example, in FIGS. 1A and 1B, the device includes a suturable material (suture ring 101) that can be secured to a tissue to further secure the device in place. In some embodiments, extension of the arms also secures the device in place. In addition, the suture ring may also be impregnated with either silver or an antimicrobial to prevent or retard infection once sutured to the skin.

In FIG. 1B, the more distal body region 102 is telescoping, and may be made of a durable, strong material (e.g., metal such as titanium) to allow the body to be extended/collapsed to distract bone or other tissue during insertion. The distal body could also be made of a composite material such as carbon fiber or plastic to prevent a galvanic response between the cartridge, therapeutic wires or silver. Alternatively, the body maybe coated or formed of a material that encourages a galvanic response to increase the overall concentration of silver ions in the region.

The body (including telescoping segments 101, 102, and 103) is a guide body that also includes a passageway into which the fiber cartridge 200 may be inserted. This body passageway (fiber outlet 103) may include one or more alignment grooves 104. The alignment grove may be used to align the fibers so that they can be extended out of the fiber outlets 103.

Figure 4A:
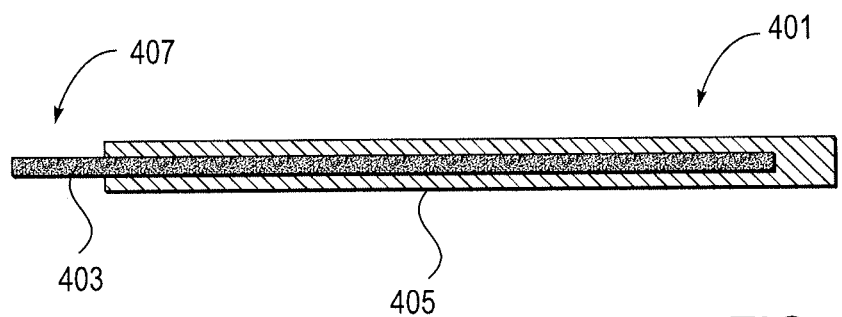
FIG. 4A shows one variation of an arm.
Figure 4B:
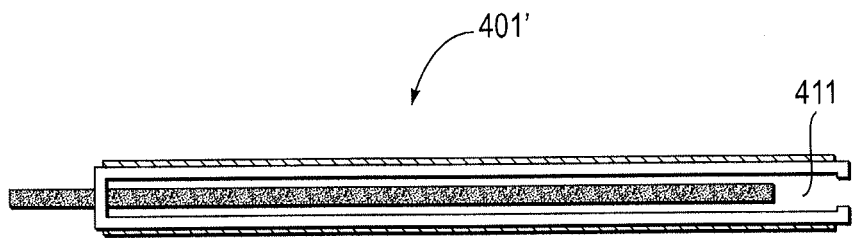
FIG. 4B shows another variation of an arm.

As mentioned, the device may include a fiber cartridge within one or more (typically 2 or more) arms that include a source of silver ions, an electrode (cathode) and a connection to the power source. In FIGS. 1A-1B the arm shown in anti-microbial agent (e.g., silver ion) releasing fiber. This arm includes a conductor extending along the arm and connecting proximally to the battery or other power source, and more distally to an electrode in contact with a source of ions. Other examples of arms include Ag fiber, Ag plated alloys (e.g., Nitinol), coated hollow fibers (polyimide (etc)), as illustrated in FIGS. 4A and 4B.

In this variation, the device includes an on-board power supply (battery 300) and electronics for controlling and/or communicating the activity of the device, such as the applied current and/or voltage, and the timing of the application of power to the arms and return electrode or electrodes (not shown). The electronics may incorporate or execute control logic for controlling the power applied to release the silver. The electronics may include hardware, software and firmware (for example, the hardware may include one or more integrated circuits for executing the control logic).

This example may also include a cap and/or spring 400 for holding the silver-release driver (battery) and/or arms in position. In some variations the battery and/or arms may be replaced in an implant after it has been inserted into the bone. For example, just the battery 300 may be replaced, or just the arms 201 may be replaced, or both may be replaced. Thus, the body (e.g., a telescoping body) of the device may remain in position.

Figure 2A:
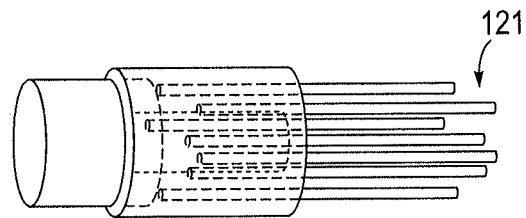
FIG. 2A shows the battery, arm housing and arms of the device of FIGS. 1A and 1B.
Figure 2B:
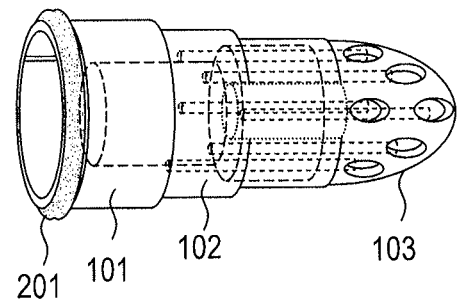
FIG. 2B shows the distal end region of the housing from which the arms may extend.

FIGS. 2A and 2B show slightly enlarged views of the battery and arms portion of the device (FIG. 2A) and the implant body (the telescoping distal end region that includes one or more openings from which the arms may be extended. The arms 121 may engage, and be guided out of the outer guide body (shown in FIG. 2B) and be deflected into their expanded (deployed) configuration, as illustrated in FIG. 1A. The arms may be deflected into position as the exit the ports (windows) in the guide body 103.

Figure 3:
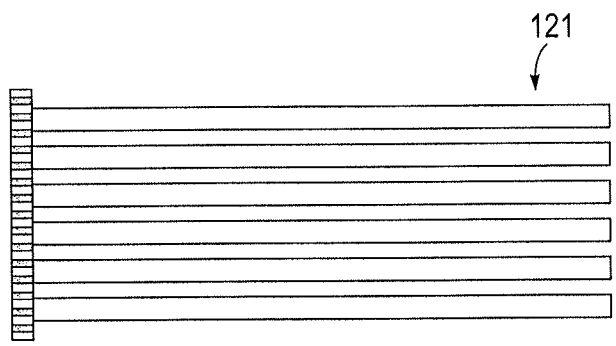
FIG. 3 shows another variation of a set of arms.

FIG. 3 shows one example of an array of arms 121 that may be used. In some variations the array of arms are individually controlled and/or connected to the power source. In other variations each of the arms (or sub-sets of arms) are grouped together. Thus, the arms may be extended (or retracted) individually or in groups. As mentioned above, the arms include a silver reservoir for release of silver ions.

FIGS. 4A and 4B illustrate two variations arms that may be used. In FIG. 4A the arm 401 includes a core wire 403 (electrically conductive) surrounded by a supporting metal 405 or structure. The support structure may be nonconductive (e.g., non-conductive polymer) of it may be conductive and insulated in parts. For example, the arm may have a support region formed of a polymer such as polyimide. In FIG. 4A, the conductor 403 may be a silver wire that is used to release ions from an exposed end region 407. In some variations the arm may include multiple release sites, preferably all long the length of the wire. For example, the outer region 405 may include openings or silver-ion permeable regions for release of silver. In some variations, the wire 403 may be coupled to another source of silver ions. In FIG. 4B the arm 401' includes one or more passageways 411 through which additional material (e.g., medicaments, etc.) may be passed into the body.

Figure 5A:
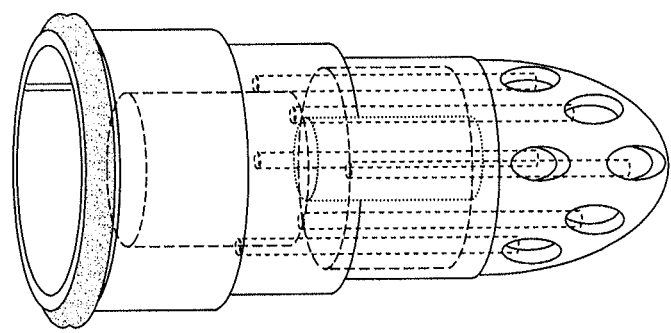
FIGS. 5A and 5B illustrate one variation of an implant in which the silver-releasing arms are retracted (FIG. 5A) and extended (FIG. 5B).
Figure 5B:
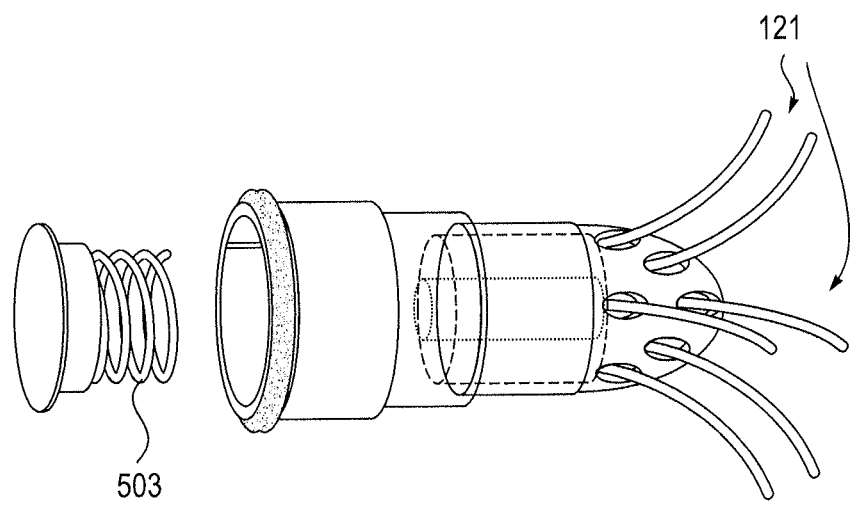

FIGS. 5A and 5B illustrate the device of FIGS. 1A and 1B before extension of the arms (seen in FIG. 5A) and after extension of the arms (seen in FIG. 5B). The arms 121 may be extended manually by advancing the proximal end region to push the arms from the distal end openings, as described above. In some variations the implant may include a biasing member 503 (e.g., a spring, etc.) holding the arms extended, and the proximal end of the implant may be capped. The cap and bias may be applied after expansion of the arms by an applicator (not shown) or they may be integral to the implant at the time of insertion/deployment.

Figure 6:
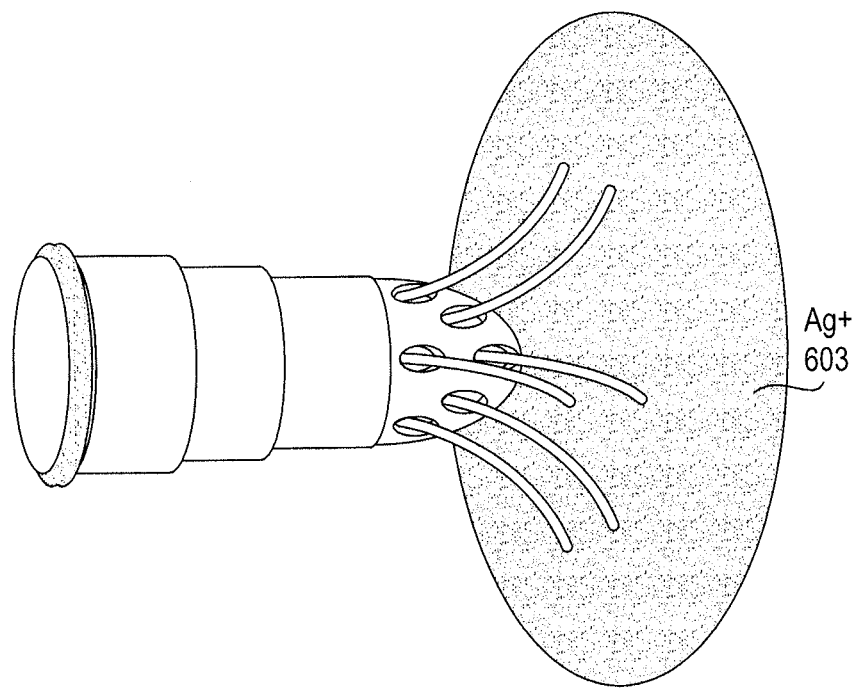
FIG. 6 illustrates one variation of the implant described herein in which the silver-releasing arms are releasing silver into the surrounding tissue.

FIG. 6 illustrates a region 603 surrounding an implanted device into which silver ions are released. In this example, the ions are released from the arms (at one or more electrodes on the arms) and pass into the body in an annular region around the implant. The return electrode in this example is on the body of the device (e.g., within or one on of the telescoping segments of the device, or at a non-telescoping outer surface of the device.

Figure 7:
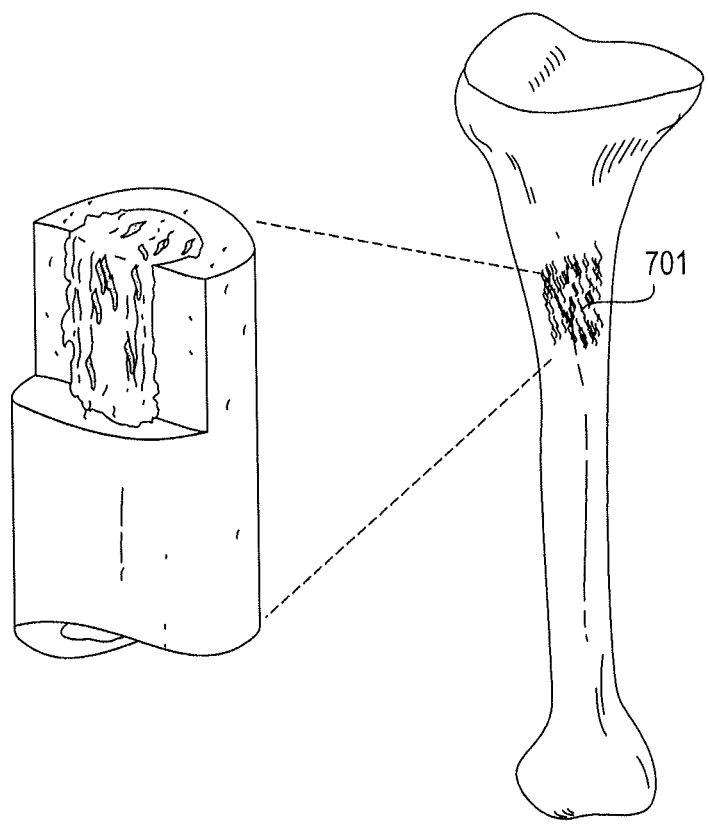
FIG. 7 illustrates a region of bone (tibia) exhibiting osteomyelitis.
Figure 8A:
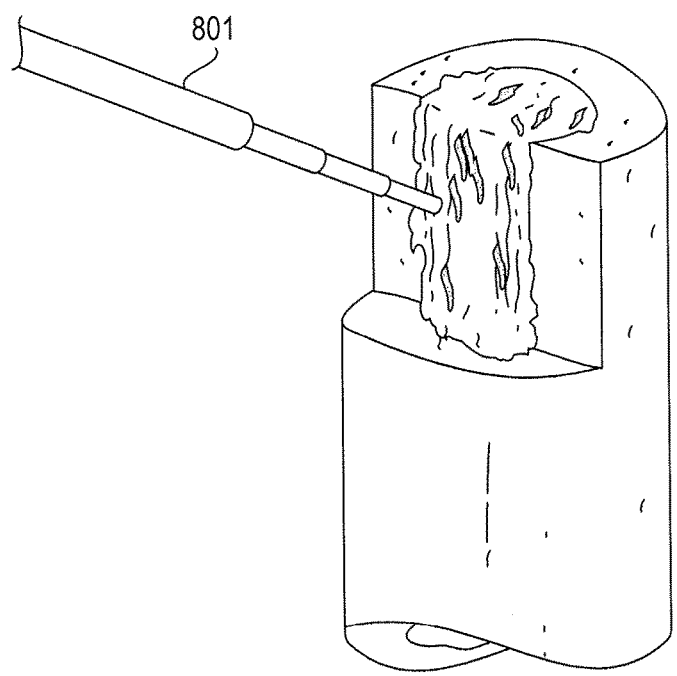
FIGS. 8A-8C illustrate insertion of an implant as described herein into the bone using a telescoping inserter.
Figure 8B:
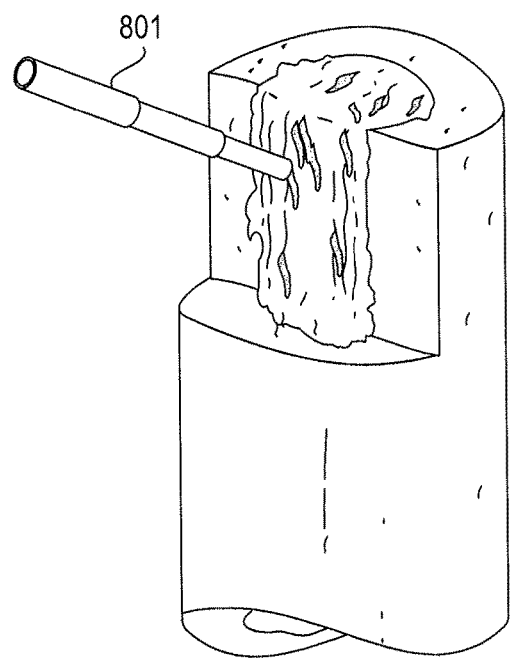
Figure 8C:
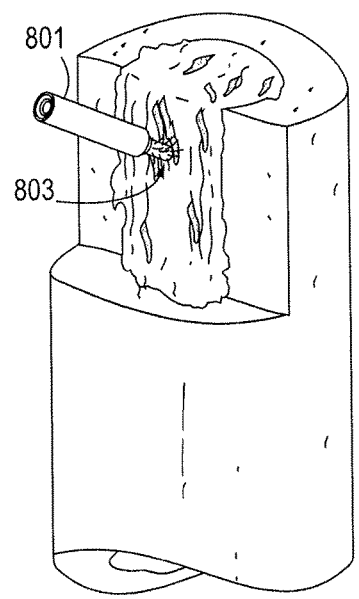

FIG. 7 illustrates an infected region of bone 701, and FIGS. 8A-8C illustrate the implantation and operation of another variation of an implant into this infected bone region. In this variation a telescoping inserter (which may be configured as a hollow body region of the implant itself) is inserted into the bone to from a passageway into the bone for the device. The implant in this example includes a "reverse telescoping cannula" 801 that is inserted into the bone. For example, a relatively small hole may be formed in the bone into the infected region so that the cannula can be inserted. Inserting the cannula initially in the extended (telescoping) configuration may allow the narrower distal end (which may include one or more openings through which the arms may be extended) to be inserted into the bone. This is shown in FIG. 8A, in which a portion of the bone has been made transparent (appearing as a cut-out) for ease of visualization. The cannula may form the outer (proximal) body of the device. Collapsing the telescoping body region of the cannula may distract the bone and/or anchor the device within the bone. An implant, including one or more extendable arms, may be passed into the cannula so that the arms can be extended from the distal end and into or around an infected region of the tissue. In FIG. 8C, the telescoping cannula (which now forms the outer portion of the implant) is collapsed down while the arms 803 are extended into the tissue. This device (including the telescoping region can be left in place to release silver for the desired time period (e.g., weeks, months). Alternatively, the telescoping region can be removed, leaving the rest of the implant behind.

Figure 9:
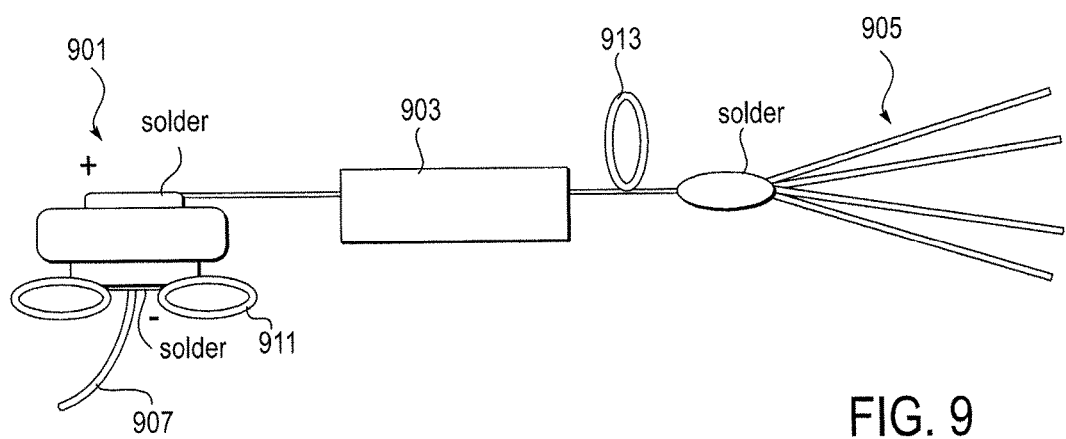
FIG. 9 shows another variation of an implant.
Figure 10A:
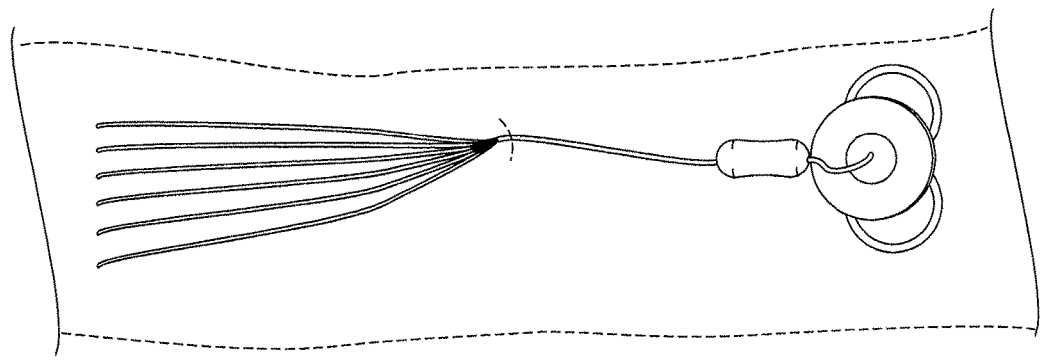
FIGS. 10A-10C illustrate the implant of FIG. 9.
Figure 10B:
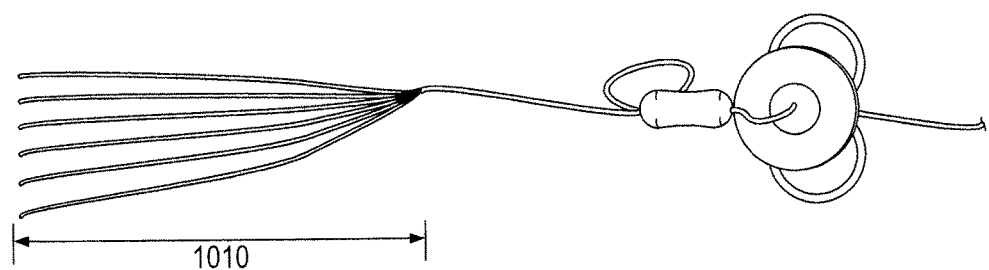
Figure 10C:
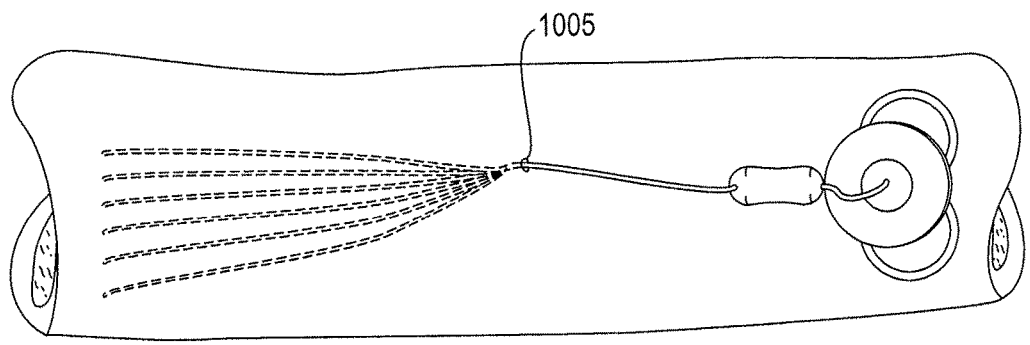

FIGS. 9-10C illustrate another variation of an implant configured for the active release of silver ions. This example was configured for use in the long bone (e.g., tibia, femur, etc.) of a mammal to treat infection. Referring to FIG. 9, a schematic of the device includes a silver-release drive (battery 901) to which a current-regulating circuit, including resistor 903 has been attached (by soldering in this example). The circuit is attached to a plurality of silver wires 905 for releasing silver ions. A return electrode (cathode 907) is connected to the opposite pole of the battery 901. The device may include one or more anchors, such as the anchoring rings 913, 911 shown on the power source and before the release source (silver wires 905), respectively.

The return electrode (cathode 907) shown in this example is a small platinum wire, however, any cathode may be used. For example, in some variations, the anchoring ring may be the return electrode. Alternatively, the cathode of the battery may be coated, or merely exposed to form the return electrode in the tissue.

In some variations, the device does not include anchoring loops, or may position the anchoring loops in other positions. For example, anchoring loops may be positioned near or in communication with the silver-releasing arms (e.g., wires).

An outer guide body (not shown) may be included over the arms (wires 905) to guide the release of the wires within the bone. The guide body may steer the wires. In variations in which the arms have a relatively low stiffness or ability to penetrate the bone without substantially deflection or deforming (as when the arms are primarily unreinforced silver wires), a template or passage-forming device may be used with the treatment implant to form the passageways into which the arms (and/or the guide body) may be inserted.

In the example shown in FIGS. 9 and 10A-D, the device includes a resistor that is calibrated so that a constant current is applied by the device. For example, a device having a 1.5 microamps of constant current has been tested in a bacterial culture, and a 15 microamp constant current variation has also been tested. Both examples displayed substantial anti-microbial activity, including forming clearings or regions surrounding the silver-releasing material in which bacteria was eliminated or substantially eliminated. The radius of clearing was roughly correlated with the current level. Even the very low 1.5 microamp current device had a comparable effect compared to the 15 microamp device, both of which produced a radius of anti-bacterial activity that were sufficient for activity in a long bone. By including multiple silver-releasing elements (e.g., wires) the radius may be expanded significantly without requiring that a higher current level be applied, potentially increasing the battery life and effectiveness of the device.

A device such as the one shown in FIG. 9 was built and tested, as shown in FIGS. 10A-10C. In this example, the battery was a lithium battery (1025 Energizer™). As mentioned above, any appropriate power source may be used, including smaller or larger batteries and external power sources. In this example, the silver wire used was a solid silver wire (99.99% silver), forming the bulk of the arm. As mentioned above, in some variations, the silver reservoir of the arm may not be a wire, but may be a spike, coil, etc., and it may be hollow, coated, or the like. For example, the arm may be a coated Nitinol or other shape memory material.

FIG. 10C illustrates the insertion of the implant into a rabbit femur. In this example, an implant such as the one shown in FIGS. 9 and 10A-B includes a four-strand silver wire braided array attached to a battery power source. The self-contained implant may be scaled for use in infected long bones, such as diabetic foot infections, where a diseased metatarsal may provide the implant site, or an infected jaw (e.g., mandible). For example, the device shown in FIG. 10B has arms having a length of approximately 5 cm. In general, the device and systems described herein may be used in any size-appropriate bone, and the implants may be sized or scaled as necessary to fit the bone.

As illustrated in FIG. 10C, the device may be implanted into a rabbit hindlimb, specifically, the mid-shaft of the tibia. In this illustration, after surgical exposure of the tibial midshaft region, an access hole 1005 was drilled from the outer bone layer into the central core of the bone (medullary cavity). A passage-forming implant device was then inserted to form passageways for the arms to insert through. In this example, the passage-forming implant includes one or more penetrator wires that are passed along the intended wire treatment wire path in the medullary bone and removed. The implant (including the array of treatment arms) was then inserted through the hole and the treatment arms into the passageways formed by the template (passage-forming) device, and the treatment device was energized, leading to continuous release of silver ions into the bone. The remaining device components (e.g., the battery and catheter) were then placed into a subcutaneous pocket within the hindlimb. In this example, the wires forming the arms have been twisted to increase their stiffness/pushability. In some variations, the arms may include another material or structure providing stiffness/pushability for implantation, even when used with a template device. The arms may be placed separately (e.g., running in different directions along the femur or other bone regions, or wrapped around the femur, etc.).

Figure 12A:
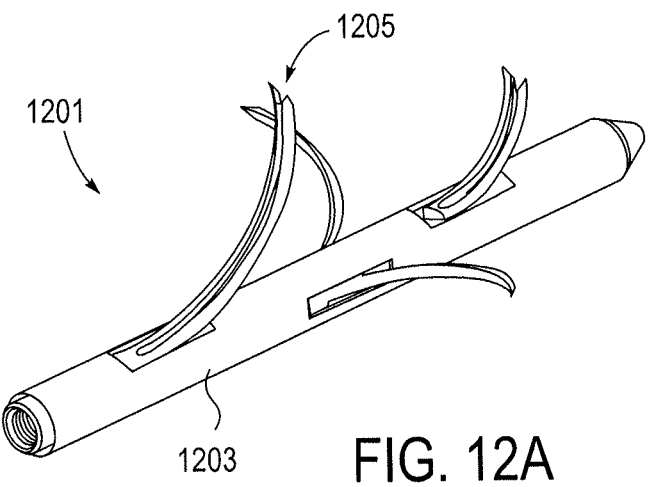
FIGS. 12A-12D illustrate another variation of an implant for releasing an antimicrobial ion.
Figure 12B:
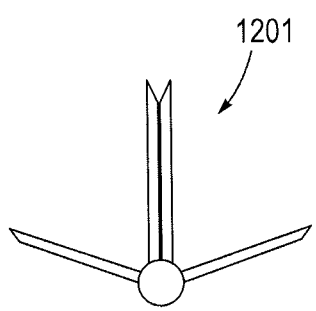
Figure 12C:
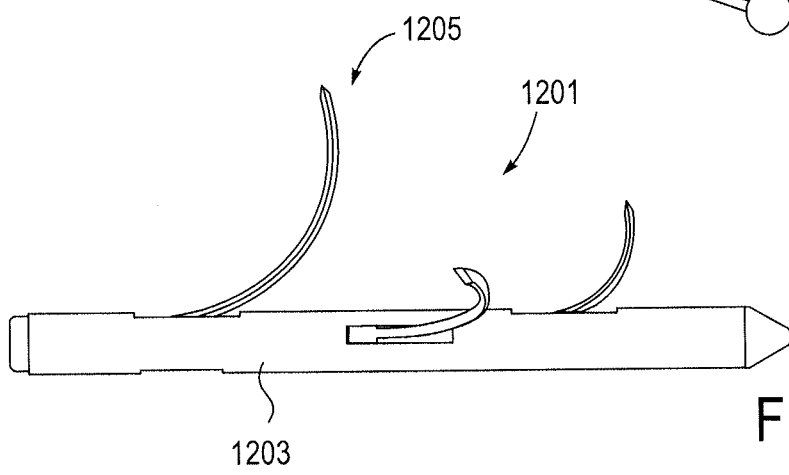
Figure 12D:
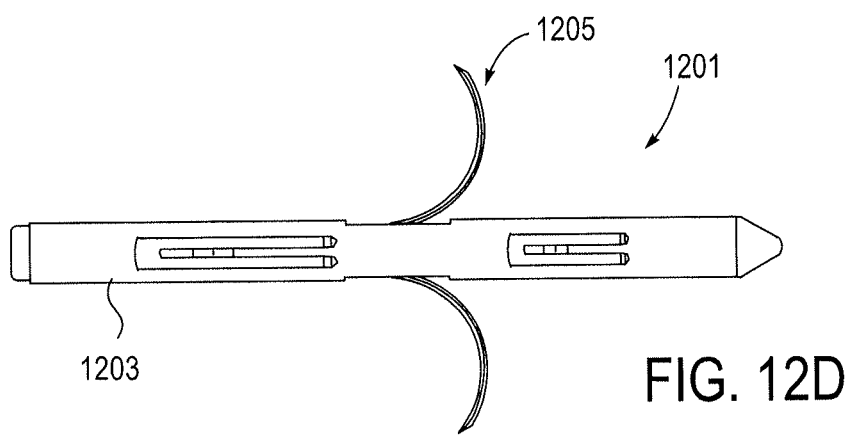

Another variation of a treatment implant is shown in FIGS. 12A-12D. This variation illustrates a silver-releasing implant 1201 that is configured for use in a vertebra to treat osteomyelitis by the electrically controlled release of silver ions. The implant in this example is formed of Nitinol, and includes a core guide body 1203 and four extendable (curved) arms 1205 that may be deployed into the bone. The deployable arms 1205 maybe be rigid and penetrating, and may be deployed, for example, into effected bony regions. In this example (as shown in FIG. 12C) the arms are shown extending from the core body region approximately 15 to 8 mm (some arms are longer than others). These dimensions, including the relative dimensions of the arms and core body region, are for illustration only, and alternative dimensions may be used, including alternative proportions. The core body in this example, has an outer cylindrical region with a tapered distal end (for penetrating bone), having a diameter of approximately 3.2 mm. In some variations, the dimensions may be varied by +/−5%, 7%, 10%, 15%, 25%, 50%, 100%, 200%, etc of the values shown. In addition, the arms may extend from the core body region in a pattern that is not uniform around the circumference of the implant, as shown in FIG. 12B, showing an end view of the implant. In this example, multiple arms extend out from the core guide body on only one side of the implant (four arms are shown, all extending in the upper 140° region).

In general, when a material such as Nitinol is used, it may be desirable to coat or treat the silver to be released onto the Nitinol frame. This is typically done by removing the passivation coating of titanium oxide on the Nitinol, which might otherwise prevent adhesion of the silver. To prevent exposure of the tissue to nickel, which may be undesirable, the nickel titanium alloy may be coated with an adhesion layer that may both passivate the nickel titanium and help adhere any silver coatings to the arms. In some variations described herein, the Nitinol may be coated or plated with an inert metal (including a conductive metal) first before plating the silver (and after removing any titanium oxide layer). Thus, the Nitinol structures (arms) including a silver reservoir may be covered with inert or biocompatible metal (e.g., gold, platinum, etc.) to encase the Nitinol, which is then coated with the appropriate silver layer. In one example, a silver-plated implant was formed by a Nitinol structure to which a gold layer was first plated followed by a silver layer.

FIGS. 13A-13E show another variation of an implant 1300 for insertion into a bone to treat infection. In this variation, the arms are slats or slat-like members that are inserted by sliding axially against a guide member and/or against each other in the distal direction; as they are slid distally, the distal ends are deflected by a deflection member (e.g., a ramp or other guide region) that is present on the guide member and on the adjacent arm(s). The arms may be collected together but able to slide axially. In some variations, the guide member may be removable after insertion of the arms, of it may be left in position within the bone, helping to hold the arms securely in position.

Figure 13A:
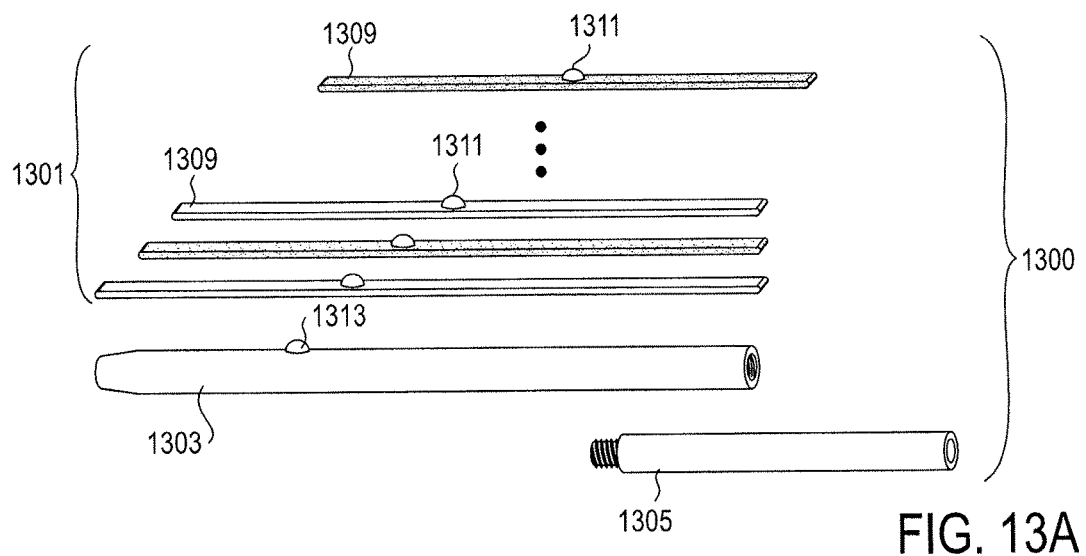
FIGS. 13A-13E show another variation of a system including a silver-releasing implant for insertion into a bone to treat infection.
Figure 13B:
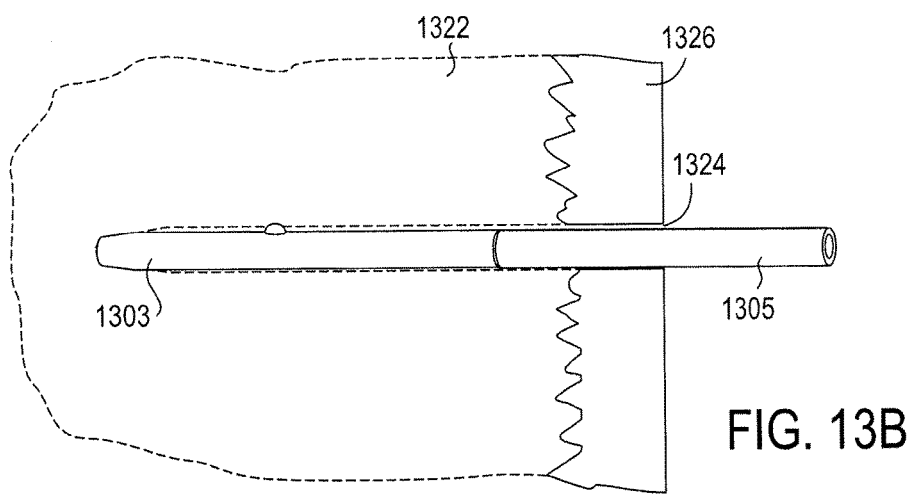

For example, in FIG. 13A, the implant includes a plurality of arms 1301, an elongate and rigid guide member 1303, and a delivery device 1305. Each of the arms 1301 is configured as an elongate member with an approximately rectangular cross-section. The arms are all configured to slide against adjacent arms or against the guide member. In general, these arms may be configured to conform to the adjacent arms or the guide member. In the example shown in FIG. 13A, the arms have flat surfaces that are configured to slide against adjacent flat surfaces on the adjacent arms or the guide member. In other variations, the arms may present curved or rounded surfaces. In some variations, the arms may include bearing surfaces (which may include additional bearing structures between adjacent arms facilitating axial motion between the arms). The arms typically include a deflectable distal region at the distal ends of the arms 1309, although the entire arm may be deflectable, or just a region (e.g., a hinge region proximal to the distal end) may be deflectable. The arms may be formed of a metal, composite, polymer, or the like (including combinations thereof). One or more reservoirs of silver are located on each of the arms. Silver reservoir(s) may be coatings. The silver reservoir may be exposed along all or a portion of the length, or in one or more discrete regions along the length. These silver-release sites may be on one or more sides of the arm. In FIG. 13A, each arm includes a deflection ramp 1311. The delivery device 1305 includes an attachment region at the distal end that is threaded for engagement with the proximal end of the guide member of the implant.

Figure 13C:
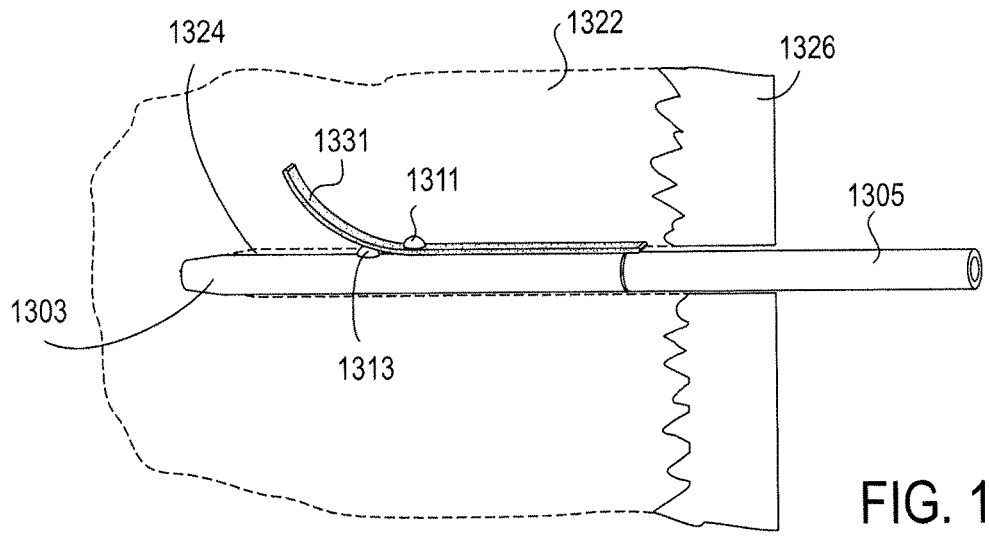

FIG. 13A is an exploded view of the implant. FIGS. 13B-13E illustrate one variation of a method for implanting the treatment implant shown in FIG. 13A. For example, in FIG. 13B, the elongate guide member 1303 is inserted into a bone. In this example, the bone is first pre-drilled to form a channel 1324 approximately the same size (or slightly larger) than the guide member 1303, through the cortical bone 1326 and into the intramedullary space (e.g., cancellous bone) 1322. The proximal end of the guide member 1303 is shown coupled to the distal end of the insertion device 1305. In FIG. 13C, the first arm member 1331 has been slid axially along the guide member and into the bone (beyond the cortical bone region 1326). The insertion device 1305 may include a pusher element that pushes the arm axially (distally) along the guide member. As the arm is driven distally, the distal end of the arm 1331 contacts the deflection member 1313, which deflects the distal end of the arm away from the long axis of the guide and into the cortical bone 1322. The distal end of the arm may be sufficiently sharp and/or tissue penetrating and/or the arm may have sufficient column strength, so that driving the arm distally pushes the distal end of the implant along a curved pathway into the cortical bone, as shown. The proximal end of the arm may be pushed beyond the cortical bone and into the intramedullary space, as shown in FIG. 13C.

Figure 13D:
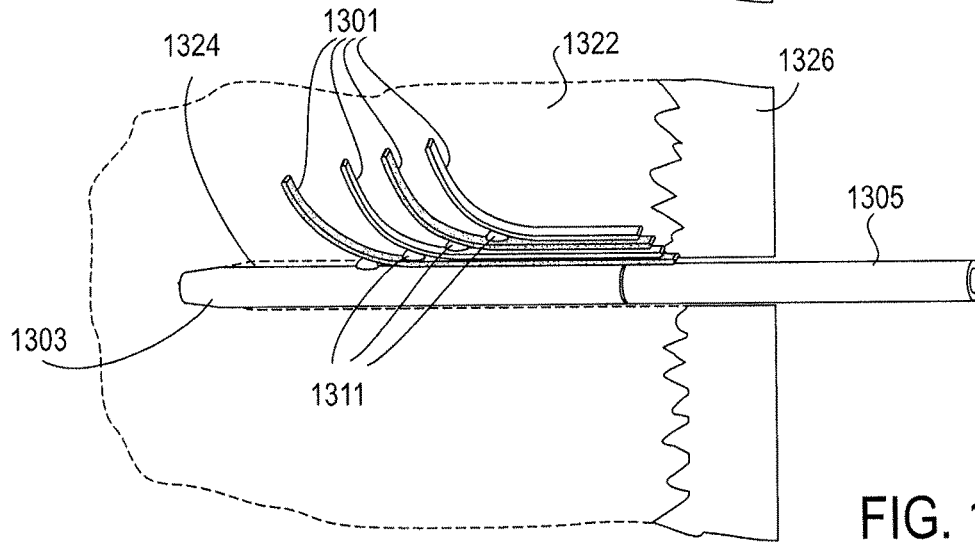

Thereafter, additional arms may be inserted by sliding distally, as shown in FIG. 13D. For example, each arm may be pushed over the delivery device (1305) using a pusher (which may be part of the device) to engage and push the proximal end of each arm. As it is slid distally, each arm may be slid along over the previous arm. The previous arm may therefore have a gently sloped proximal end (not shown) to allow gradual loading onto the arm by a new arm; each of the previous arms also typically includes a deflection element (e.g., a ramp or protrusion) that deflects the distal end of the adjacent arm being loaded in a curved pathway through the bone. The deflection element may be positioned at some portion of the upper surface of the adjacent arm. In some variations the arms have decreasing lengths so that they all end (when fully implanted) near about the same proximal portion of the implant; in other variations the proximal ends are staggered so that the later-applied arms terminate more distally or more proximally (as shown).

FIGS. 13A-13D illustrate an implant that project (in the delivered configuration) into the bone from only one side of the guide member. In some variations, the device may be configured to project into the bone in different directions (e.g., on the bottom of the inserter in FIG. 13D). The variation shown in FIGS. 14A-14C illustrates one embodiment of this.

Once inserted, the implant may be activated (or may be inserted in the activated configuration) to release silver over time. For example, a silver-release driver may be coupled to each arm to drive release of silver from the silver reservoirs on each arm. In some variations a single electrical drive (e.g, power source) is located within the guide member and electrical contact is made with each silver reservoir (not shown). For example, electrical contact may be made through the deflection members that may engage complimentary electrical contacts on the bottom of each arm when inserted into the bone. In some variations each arm is separately coupled to an individual silver-release driver. For example, the silver reservoir on each arm may be coupled to a galvanic reactor metal or a power source driving release of silver ions.

In some variations, the implant includes a collar or link around or between the arms, holding them together, even as they are axially movable or slideable relative to each other. For example, one or more collars may collect the implant arms together. The collar may also hold the guide member relative to the arms. The collar may be coupled to the silver-release driver.

Figure 13E:
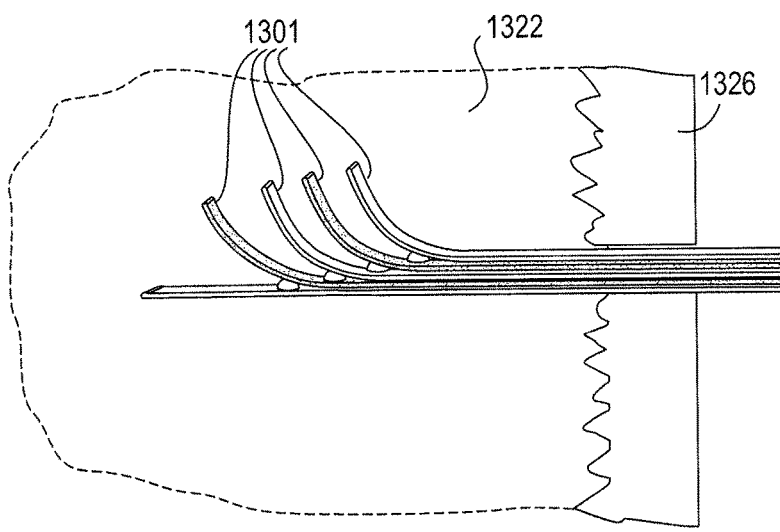

FIG. 13E illustrates one method of removing the implant of FIG. 13A. In this variation, the guide member may be removed from the bone leaving a passage from which each arm 1301 can be withdrawn. A removal tool (e.g., having a grasper or engager to couple with the proximal end of each arm or a plurality of arms) may be used to remove the arms and thus the implant.

FIGS. 14A-14D show another variation of an implant having arms including a deflection member along their length for deflection of adjacent arms as the arms are inserted axially. FIG. 14A shows an exploded view of the implant 1400, including a plurality of arms 1401, a guide member 1403. A portion of an inserter 1405 is also shown. FIG. 14B illustrates the implant assembled and in a deployed configuration, with the arms extending outwards. In this variation, three sets of arms are shown, each with at least one silver reservoir for release of silver (not shown). Each set is configured so that the arms may be extended axially to project the arms into the bone and be stacked and slid relative to each other so that the more radially (outer) arms are deflected by the adjacent arms. In FIG. 14C, an end view of the deployed implant shown a variation in which the arms are grouped into three sets positioned around the perimeter of the centrally located guide member. In this variation, the arms are stacked atop one another. An alternative deployed configuration is shown in FIG. 14D, in which the more outwardly-located arms in each set are staggered slightly along the perimeter of the guide member. This configuration may provide a slightly broader expanse of arms in the deployed configuration. As mentioned above, adjacent arms may be configured to slideably mate; in some variations the configuration may allow for both the radially outward deflection, expanding the arms into the bone, and they may also drive them to be offset around the circumference as shown in FIG. 14D. For example, the upper surface may include a track or lateral deflector.

Figure 15A:
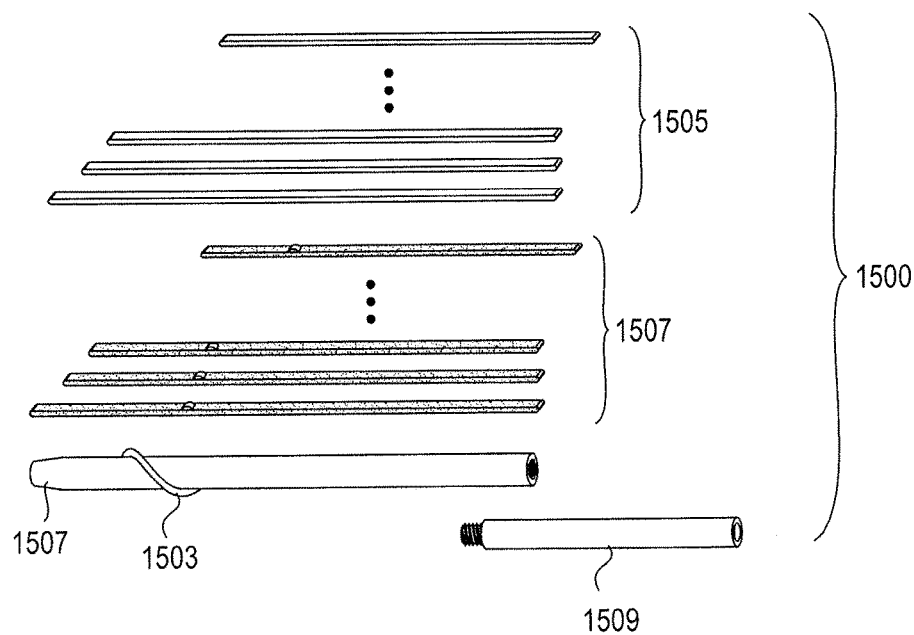
FIGS. 15A-15C show another variation of a system including a silver-releasing implant for insertion into a bone to treat infection.
Figure 15B:
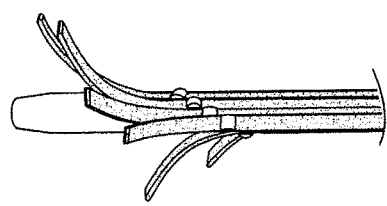
Figure 15C:
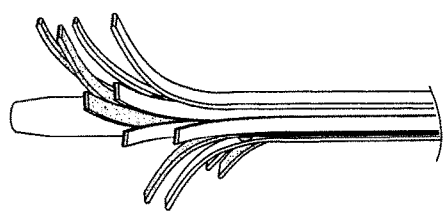

FIGS. 15A-15C illustrate another variation of an implant 1500 similar to that shown in FIGS. 13A and 14A; a portion of an insertion device 1509 is also shown. In this example, the guide member 1507 includes a spiral-shaped deflection region 1503. Two sets of arms 1503, 1505 are included, each set including a silver reservoir (not shown). The first set 1505 also includes a deflection element (e.g., ramp) along its length. The second set of arms 1503 may be slid distally along arms of the first set 1505. FIG. 15B shows the implant after deployment of the first set 1505 of arms over the guide member 1507. FIG. 15C shows the implant after deployment of the second set 1503 of arms over the guide member 1507 and the first set of arms 1505.

FIGS. 16A-16C illustrate another variation of an implant having a plurality of deflectable arms that are extended from the implant by a deflection element on the guide member 1601. In this variation, the implant includes a guide member 1601 having a deflection member configured as an annular ring 1603. The arms 1605 are arranged around the perimeter of the guide member in two concentric rings, as shown in the cross-sectional view of FIG. 16C. Each arm is axially slideable distally, relative to the guide member 1601 and/or an adjacent arm. In some variations the implant in the undeployed (e.g., delivery) configuration has the arms pre-arranged around the central guide member 1601. The arms may be collared or otherwise secured to hold them around the circumference of the guide member, while allowing them to extend axially for deployment and expansion by deflection over the deflection element 1603 located distally on the guide member 1601. To deploy the arms of the guide element (e.g., within the bone), the rings of arms may be collectively or individually slid distally, axially along the length of the inner guide member 1601.

In any of the variations shown in FIGS. 13A, 14A, 15A and 16A, the arms and the guide member may be coupled together in the undeployed configuration, or they may be unassembled until they are being deployed. Also, in any of these variations any of the elements previously described (including the silver-release driver) may be included. These devices may also be removed from the bone, as mentioned above.

In some variation, the device may be configured so that, upon removal from the bone, they automatically remove or sample a region of the bone (e.g., by "coring" a portion of the bone). Any samples removed may be examined to determine the effect of the implant, including determining the presence or absence of infection. For example, in some variations the guide member or the arms, or some other portion of the device, includes a coring element that is oriented so as to remove a tissue sample (e.g., bone sample) when the implant or portion of the implant, is removed. FIGS. 17 and 18 illustrate variations including sampling members.

FIG. 17 shows a variation of an arm having a two sampling regions 1701, 1703. This arm, or a plurality of similar arms, may be included in any of the variations described above, particularly those shown in FIGS. 13A, 14A, 15A and 16A. For example, the outermost (radially) arm in any of these variations may include the sampling arm shown in FIG. 17. Withdrawing the sampling arm proximally from the bone may result in removing of a sample (core) that is collected into the sampling regions 1701, 1703.

In FIG. 18, another variation of an implant is shown in which the arms have been extended into the deployed configuration into a bone. In this variation, the implant includes a plurality of sampling elements 1801 on many (if not all) of the arms and the guide member.

Figure 19A:
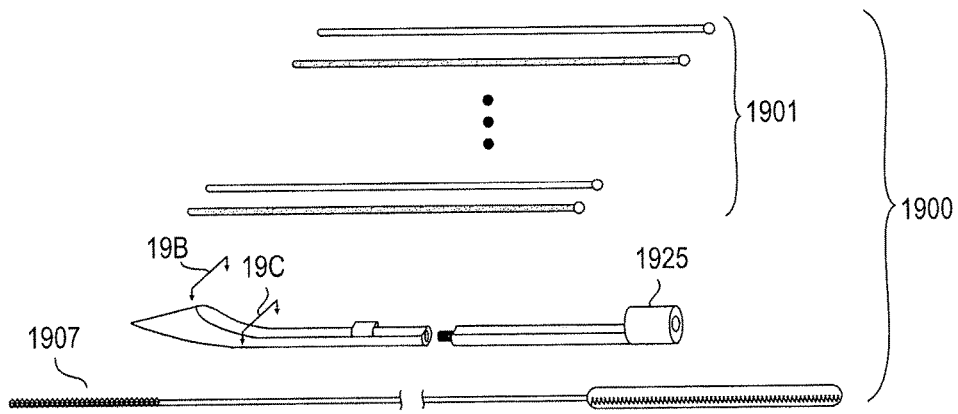
FIGS. 19A-19E illustrates one variation of a system including a silver-releasing implant for insertion into a bone to treat infection.
Figure 19B:
Figure 19C:
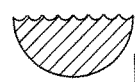
Figure 19D:
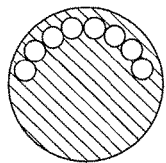
Figure 19E:
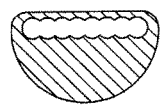

FIGS. 19A-19L illustrate another variation of a system including a treatment implant and a template or passage-forming device for pre-forming the passageways through the bone into which the arms of the treatment implant will be inserted. FIG. 19A shows an exploded view of the system 1900, including a plurality of arms 1901, a guide member 1905 and a pre-bore stylus 1907. The pre-bore stylus is the passage forming device that may be used with the guide member to form the passageways into the bone in which the arms 1901 may be inserted.

In this example, the guide member is a rigid elongate member (although non-rigid members may be used) that includes multiple guide regions, such as channels, along the device for directing the implant's silver-releasing arms out of the device. In the example shown in FIG. 19A, these guide regions are open channels, as illustrated in the cross-sections through the guide member in FIGS. 19B and 19C. In an alternative embodiment, these channels may be closed channels, as shown in alternative cross-sections 19D and 19E.

In operation, the system may be used as illustrated in FIGS. 19F-19L. Initially an insertion channel may be drilled into the bone, and the guide member inserted. The guide member may be anchored into position in the bone. For example, the guide member may have extendable anchors (not shown). In some variations the guide member may be secured (e.g., so that it doesn't move or rotate relative to the bone once secured) in the channel at the proximal end, for example at the cortical bone entry site or to the outside of the bone. In some variations, the guide member is secured within the bone by a bone cement. In some variations (similar to that shown in FIGS. 19A-19I), the implant guide member is coupled to an insertion tool 1925 and the insertion tool may be anchored rather than (or in addition to) the guide member 1905. The anchoring may be releasable so that all or a portion of the implant (or the insertion tool) may be released from the bone for removal.

Figure 19F:
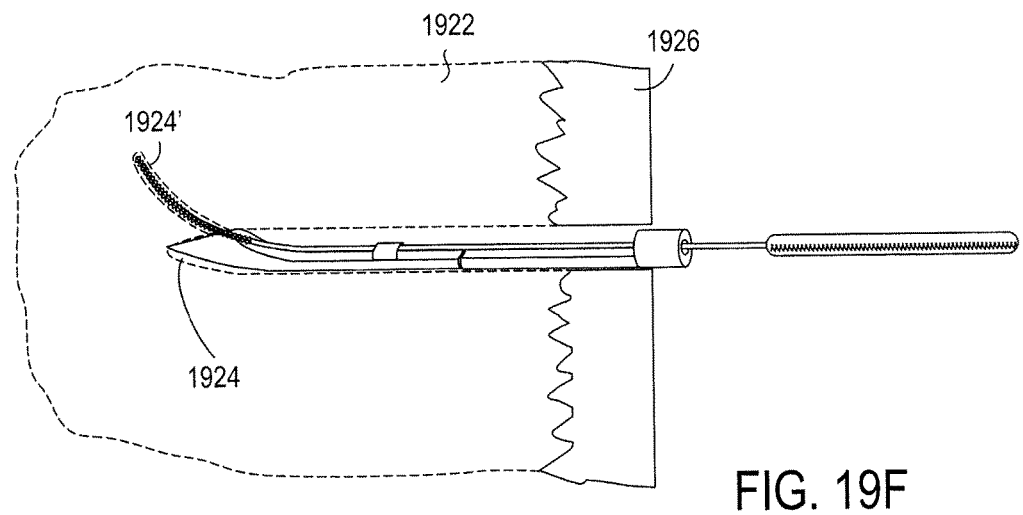
FIGS. 19F-19J illustrate insertion of the implant shown in FIG. 19A.

As illustrated in FIG. 19F, once the guide member is in position within the bone 1922 (past the cortical bone 1926) in a central channel 1924, channels into the bone for the placement of the arms 1924' may be formed using the elongate pre-bore stylus. In FIG. 19F, a single pre-bore stylus may be driven along each pathway through the guide member to form a channel for each arm. Alternatively, a pre-bore stylus may have multiple tissue (bone) penetrating members that can be guided into the bone to form the passageways. The pre-bore stylus may be a bone-penetrating member having a sufficient column strength to penetrate the bone. In some variations it may be a cutting tool, including electrical cutting tool (e.g., electrosurgical), or a drilling tool. The diameter of the pre-bore stylus or other template device channel-forming component may be approximately the same or slightly smaller than the diameter of the arms, or in some variations, larger.

Figure 19G:
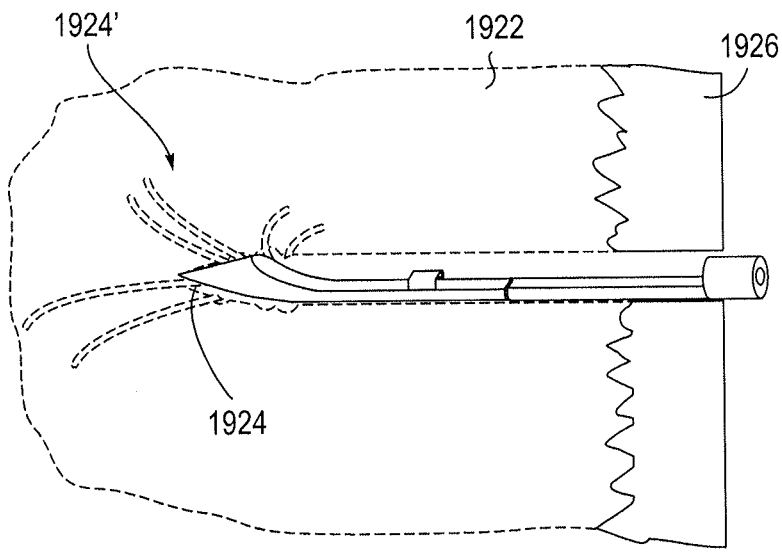
Figure 19H:
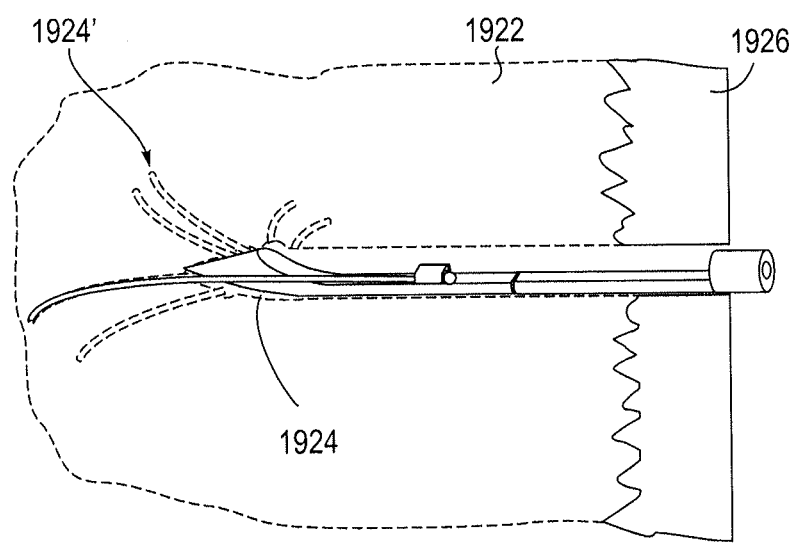
Figure 19I:
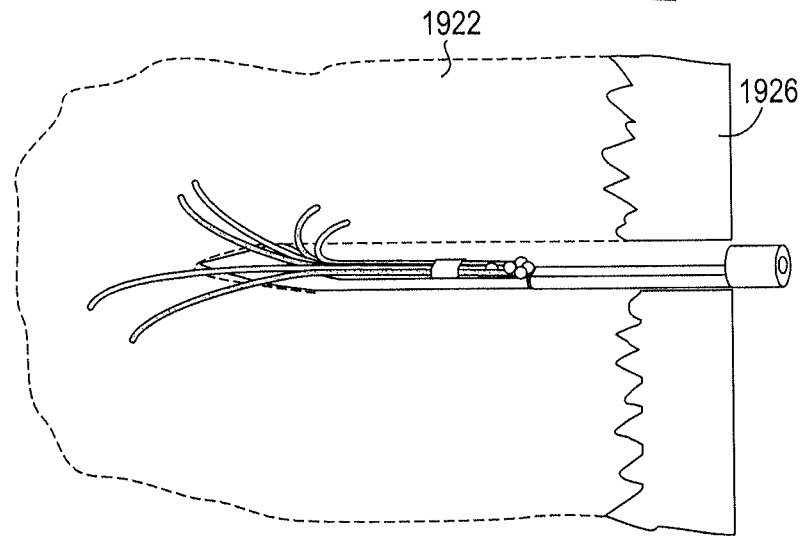

Once the channels have been formed, as illustrated in FIG. 19G, the implant's silver-releasing arms may be inserted. The arms may be individually inserted (as shown in FIGS. 19H-19I), or they may be inserted all together, in variations in which the arms are coupled together. The guide may then direct the arms as they are each slid distally in the guide channel(s) through the channels formed by the template channel-forming tool, until they are fully extended, as shown in FIG. 19I.

Figure 19J:
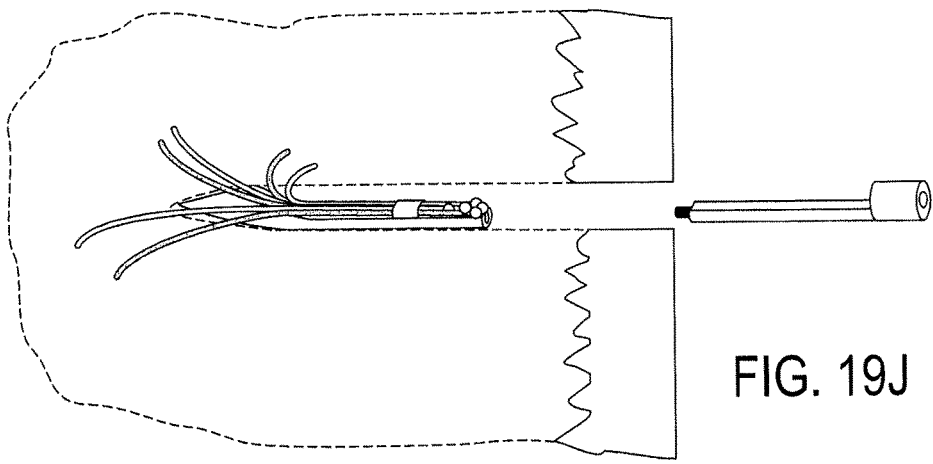

In some variations the implant is coupled to an inserter 1925 for insertion. In the variation shown in FIGS. 19A-19I, the insertion device is shown partially illustrated and coupled to the guide member. The inserter extends the guide channels of the guide member. In FIG. 19J, the inserter is removed from the proximal end of the implant, and the implant may be left in position. The hole into the bone may be filled or capped, although access may be left available to retrieve or alter the implant later. The extended arms may help anchor the device in place, though it may be removed in whole or in part, as illustrated in FIGS. 19K and 19L.

Figure 19K:
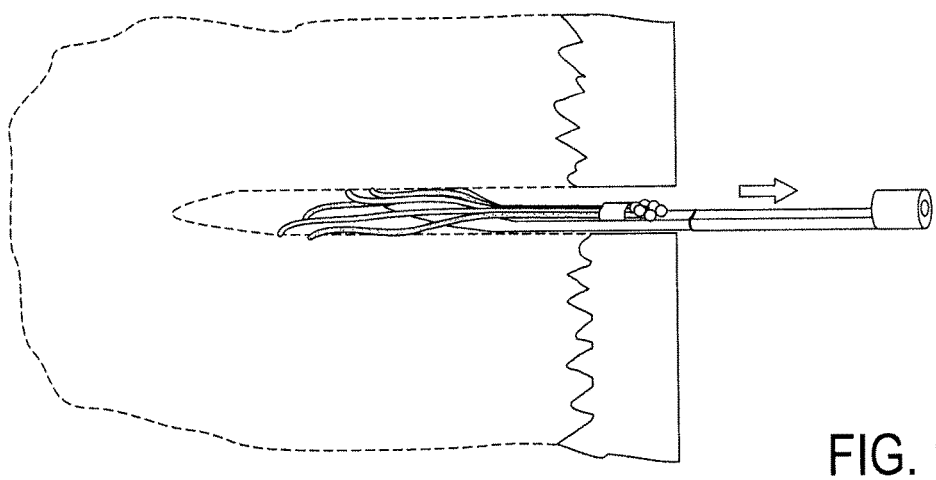
FIGS. 19K and 19L illustrate various methods for removing the implant of FIG. 19A.

In FIG. 19K, the entire implant is removed by again coupling the proximal end of the guide member to an inserter device, or to a removal device that is complementary to the coupling region on the proximal end of the inserter, and drawing the implant proximally out of the bone.

Figure 19L:
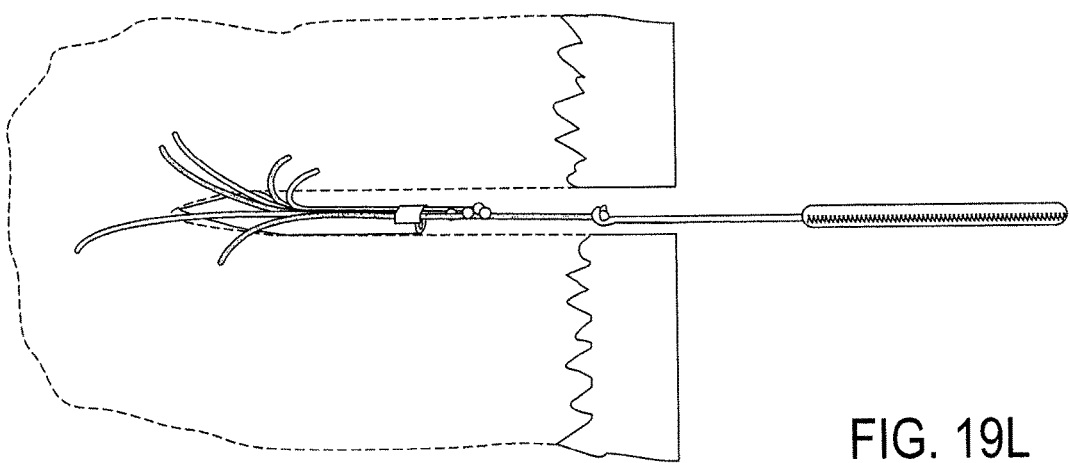

Alternatively, in one variation, as shown in FIG. 19L, the individual (or a group of) the arms may be removed using an arm removal device. In the example shown in FIG. 19L, the guide member has been separately removed, although in some variations, the guide member may be left in position. An arm removal device may include a coupling region that couples to the proximal end of an arm or a group (including all) of the arms. In FIG. 19L the implant arms include a ball region at their proximal ends, and the removal device includes a coupling member that clamps or otherwise grasps the proximal end.

Figure 20A:
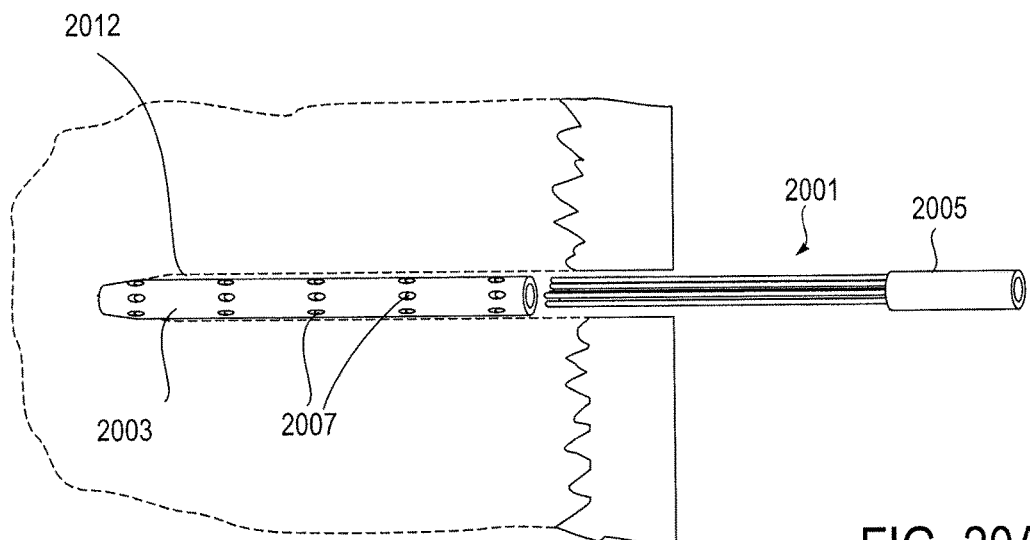
FIGS. 20A and 20B illustrate another variation of a silver-releasing implant for insertion into a bone to treat infection.
Figure 20B:
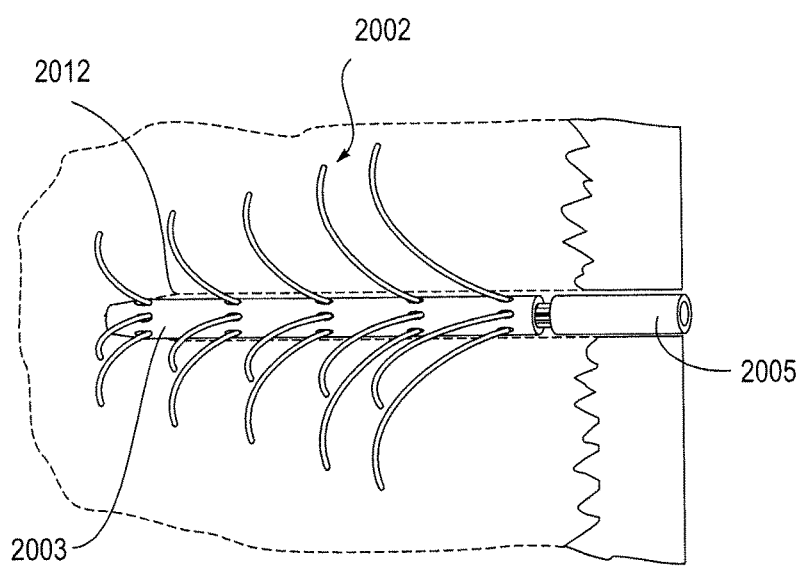

Another example of a silver-releasing implant is shown in FIGS. 20A and 20B. In this example, the implant includes a guide member 2003 having a plurality of guide channels and openings 2007 at various positions along its length. The guide member may be inserted into the bone channel 2012 as described above, and the arm assembly 2001 including a plurality of silver-releasing arms (e.g., arms having silver depots) may be inserted into the guide member so that the arms are guided along the length of the guide member and out into the bone from various positions and at various angles relative to the guide member, as illustrated in FIG. 20B. The proximal end of the arm assembly in this example includes a housing that may include the silver-release driver. The housing may also be configured to couple to an inserter/remover (not shown), including a releasable attachment region (e.g., a threaded attachment region, a snap-fit attachment region, etc.). In some variations, the distal end of the housing also includes an attachment region for mating with the distal end of the guide member.

In some variations the treatment implant includes a replaceable or rechargeable silver-release driver. For example, FIGS. 21A-21D illustrate an system 2100 including an implant having a guide member 2103, a plurality of silver-releasing arms 2101, and an endpiece 2105 that includes a power supply for driving release of the silver ions. The endpiece 2105 may include a flange rim 2097 securing it to the bone surface, as well as an attachment site 2111 for coupling to the implant (e.g., the plurality of arms). The end piece may be secured to the implant once it has been placed and expanded using an inserter, as mentioned above. The end piece may also include an access 2109 for a batter replacement, such as a cartridge, door, panel, etc.

Figure 21A:
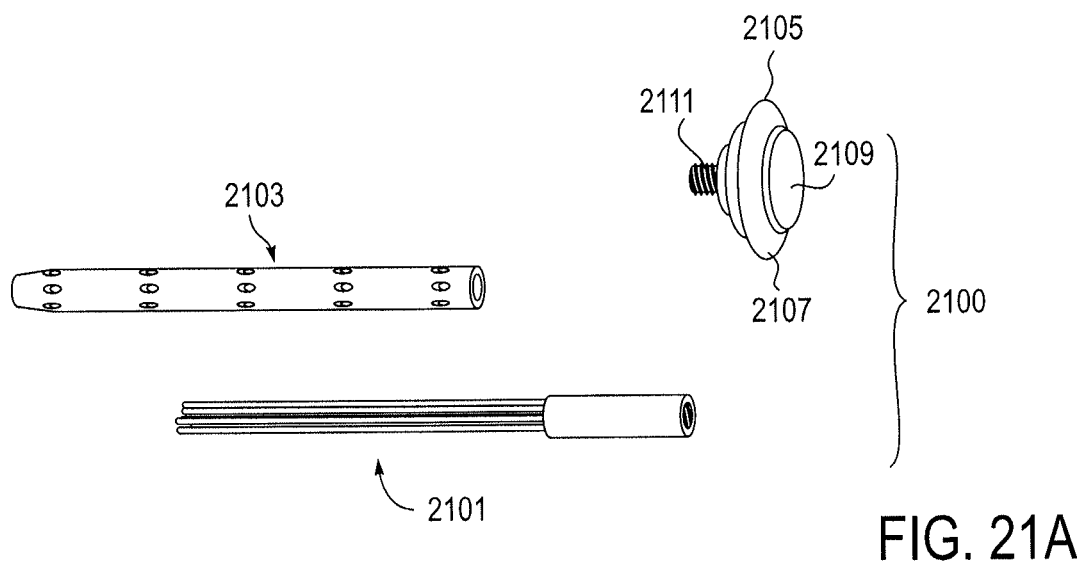
FIGS. 21A and 21B illustrate another variation of a silver-releasing implant for insertion into a bone to treat infection.
Figure 21B:
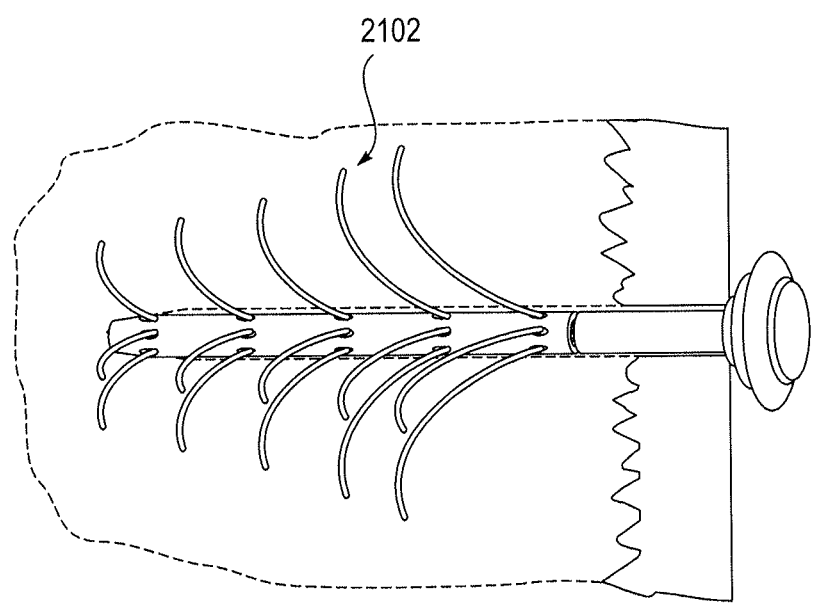
Figure 21C:
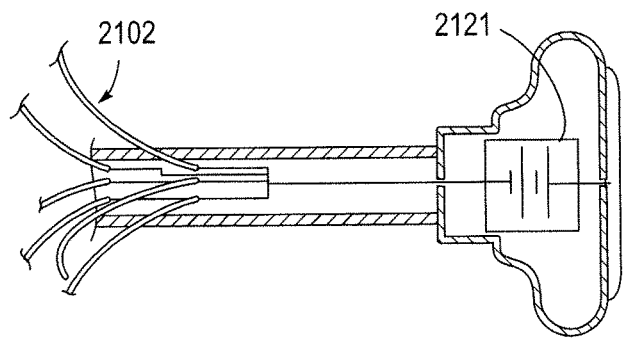
FIG. 21C shows a cross-section through the implant of FIG. 21A.
Figure 21D:
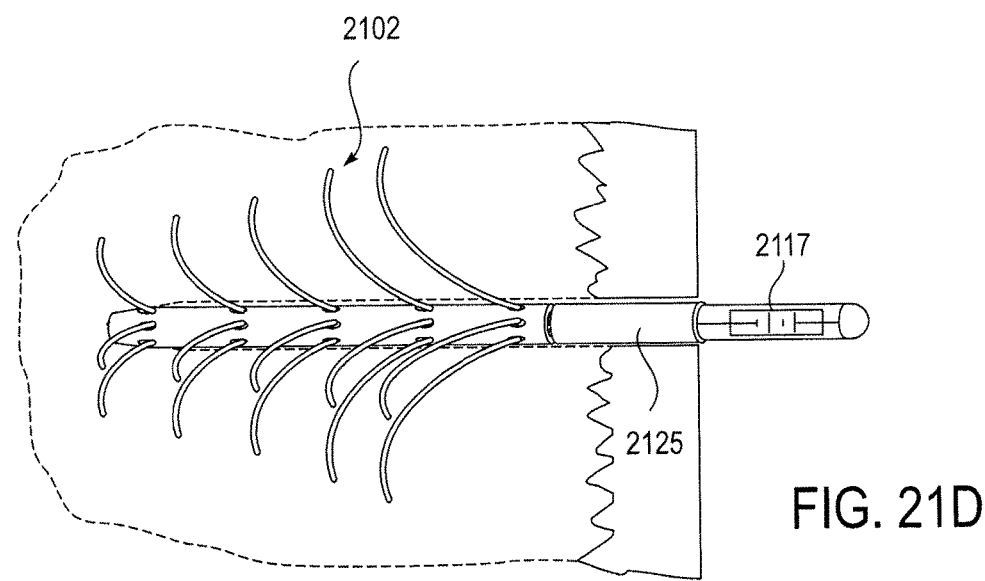
FIG. 21D shows an alternative variation of the implant of FIG. 21A.

FIG. 21B illustrated the variation shown in FIG. 21A after implantation into the bone, in which the arms 2102 have been extended from the guide member. FIG. 21C shows a cross-section through the implant, schematically illustrating the electrical connections to the arms 2102 and the battery element 2121. FIG. 21D illustrates an alternative embodiment, in which the silver release driver 2117 is insertable within the device (e.g., the housing 2125 of the plurality of arms).

Figure 22A:
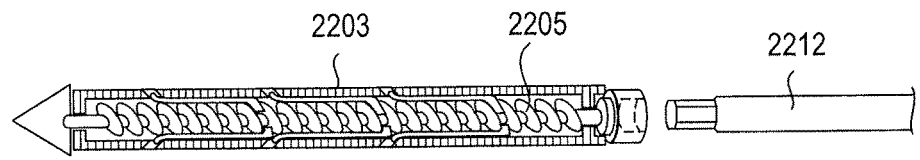
FIGS. 22A and 22B illustrate another variation of a silver-releasing implant for insertion into a bone to treat infection and an insertion/activation device.
Figure 22B:
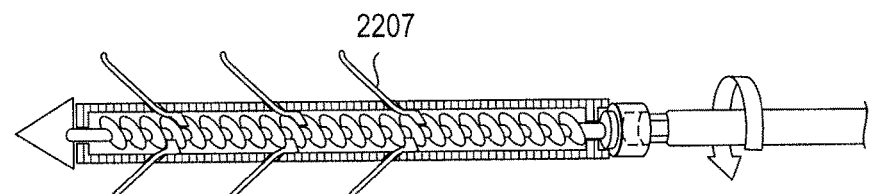

In some variations the arms of the implant may be controllably extendable/expandable from the implant guide member by activation of a control element. For example, in FIGS. 22A and 22B, one variation of a silver-releasing implant is shown in which the arms of the implant are configured to be extended from a guide body 2203 by rotation of an internal extension/retraction mechanism 2205 to push (or pull when retracting) the arms 2207 from the guide member and into the bone. In this example, a tool (an extension tool) 2212 may be used to turn the internal mechanism. The internal mechanism is shown as an Archimedes-screw type mechanism that drives linear motion (forward/backward axially) of the plurality of silver-releasing arms. Other variations may also be used to control extension and/or retraction of the arms. In some variations an external tool is not required, and the device automatically (or under remote control) extends or retracts the arms. The arms may be fully extended from the guide member, or they may be gradually extended to gradually expose more silver (or to replenish depleted silver from the distal ends of the arms).

Figure 23:
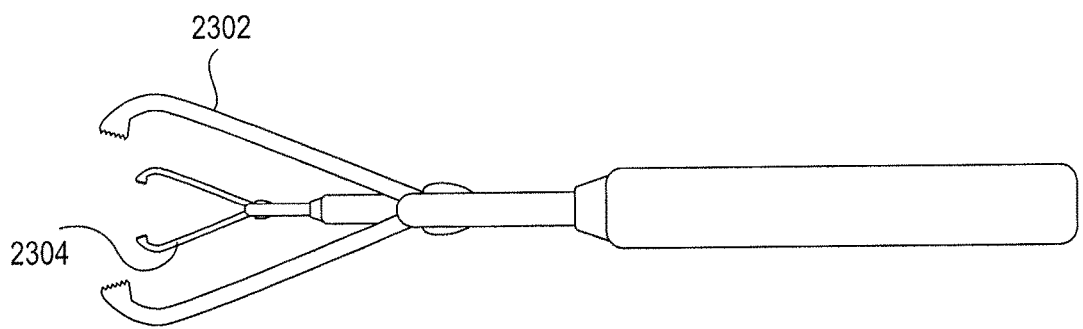
FIG. 23 illustrates one variation of an implant inserter and remover.

As mentioned above, in some variations the implants maybe removed in whole or in part from the bone. In some variations, the insertion tool or device may also be used to remove the implant. In some variations a separate or dedicated removal device may be provided. For example, FIG. 23 illustrates one variation of a removal device. In general, a removal device may include a pair of engagement regions for individually engaging both the guide member of the implant and the plurality of arms of the implant. In FIG. 23, an outer engagement member 2302 is configured to engage the guide member at the proximal end of the guide member, while an inner engagement member is configured to engage the plurality of arms. In this example the engagement members are clamps or jaws that controllably engage either the guide member or the plurality of arms. Other engagement members may be used for coupling with complimentary coupling regions on the implant. As illustrated above, the coupling region on the guide member and a coupling member on the plurality of arms may be a threaded region that engages a threaded member(s) on the removal device. Threaded regions on the plurality of arms and the guide member may be oppositely threaded.

In the exemplary device shown in FIG. 23, the inner coupling member (engagement member 2304) for coupling to the plurality of arms may be separately controlled relative to the outer coupling member (engagement member 2302) for coupling to the guide member, allowing the retraction and possibly removal of the arms relative to the guide member. In operation, the removal device may move the arms relative to the guide member (leveraging off of the guide member) to collapse the arms.

Figure 24A:
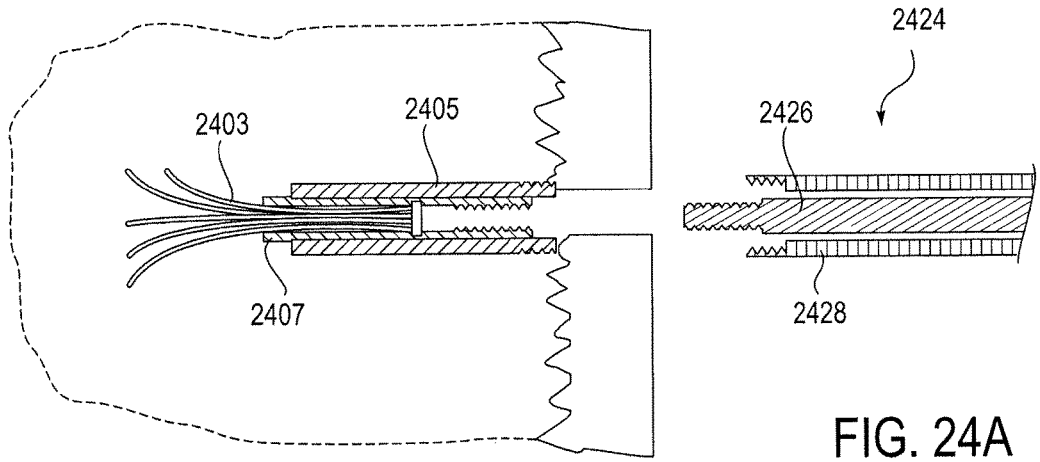
FIGS. 24A-24E illustrate removal of one variation of a silver-releasing implant, as described herein.

FIGS. 24A-24E illustrate removal of another variation of a silver-releasing implant. In this example, the implant has been inserted into the bone and a plurality of arms extended into the bone. The arms 2403 extend from the distal end of the housing/guide member 2405. In FIG. 24A, the plurality of arms are coupled together in an inner member 2407 that can be advanced/retracted within the guide member 2405. The proximal end of the inner member includes a coupling region (threaded in this example), while the proximal end of the outer member (the guide member 2405) also includes a coupling region. In this example, a removal device 2424 includes an inner coupling member 2426 for coupling to the plurality of arms at the coupling region on the inner member 2407. The removal device also includes an outer coupling member 2428 for coupling to the guide member 2405. It should be noted that in some variations the role of the outer and inner members may be reversed (e.g., the outer member may couple to the plurality of arms and the inner member may couple to the guide member). In some variations the two coupling members are not arranged concentrically, but are arranged side-by-side.

Figure 24B:
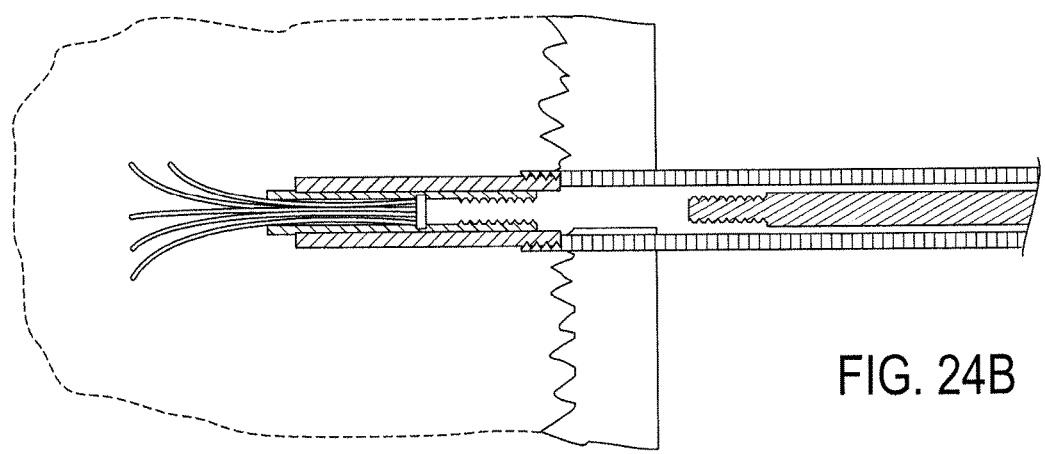
Figure 24C:
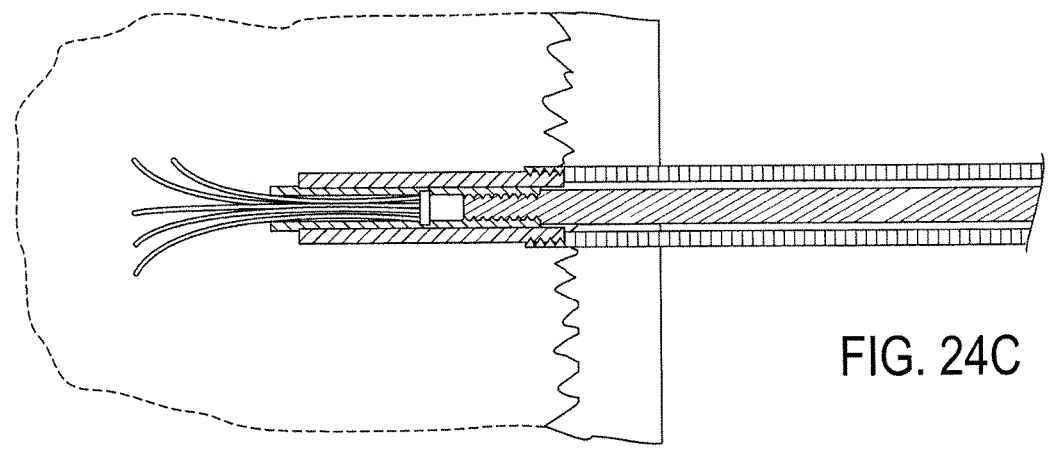
Figure 24D:
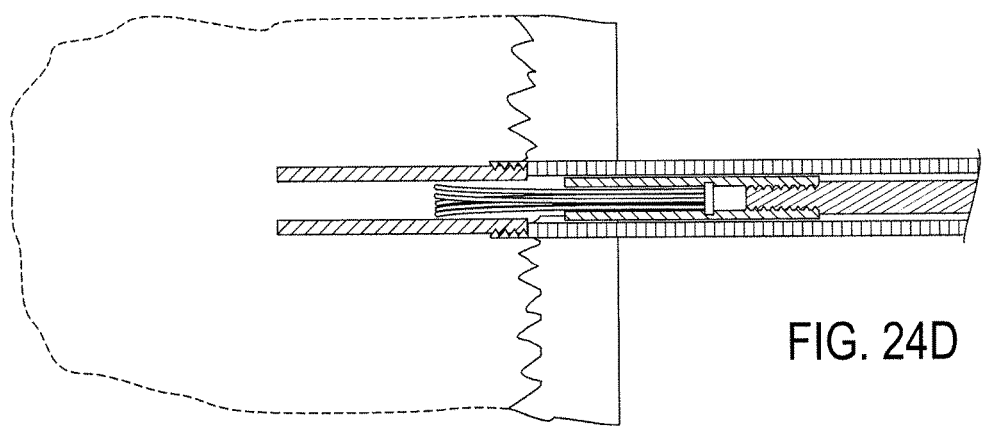
Figure 24E:
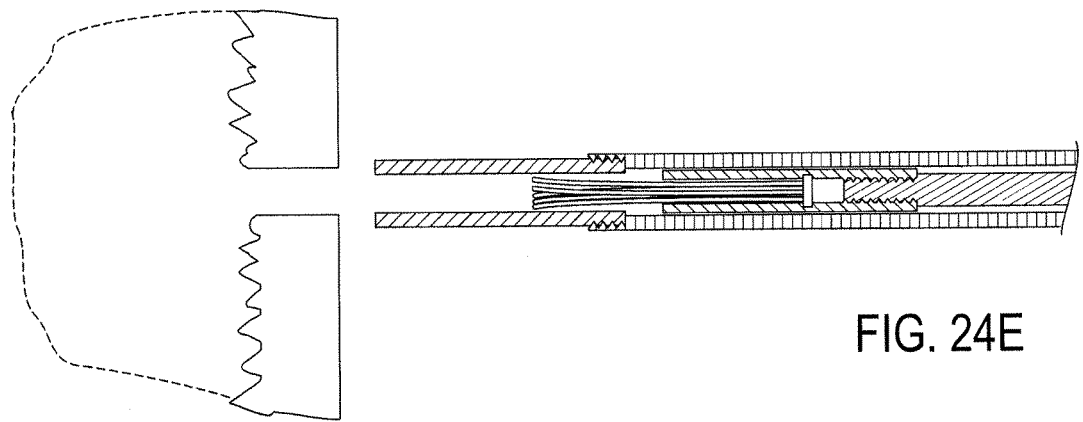
Figure 25:
FIG. 25 shows one variation of a coupling region that may be used as a connector.
Figure 26A:
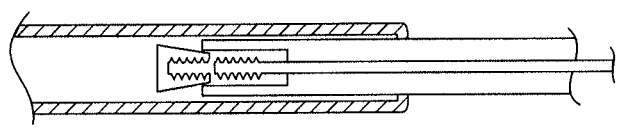
FIGS. 26A and 26B illustrate another coupling structure and method of coupling.
Figure 26B:
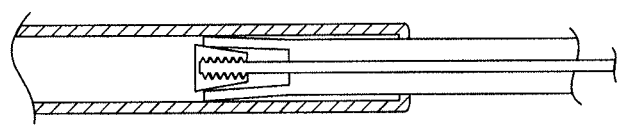
Figure 27A:
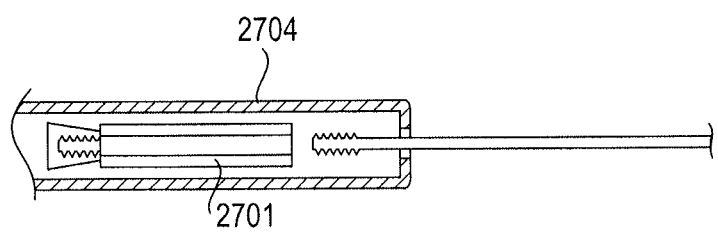
FIGS. 27A and 27B illustrates the coupling means shown in FIGS. 26A and 26B expanding an inner member within a surrounding outer member.
Figure 27B:
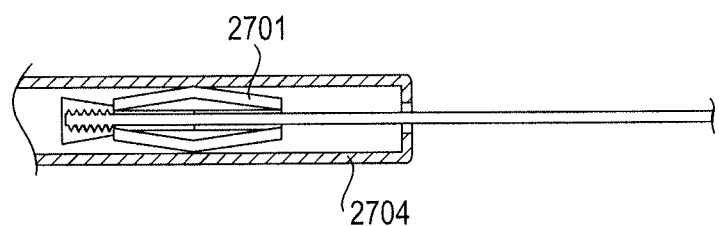

In FIG. 24B the outer coupling member has been coupled to the threaded region on the guide member. FIG. 24C shows the coupling of the inner member to the plurality of arms. The plurality of arms can then be drawn proximally, withdrawing them from the bone, as shown in FIG. 24D. Finally, in FIG. 24E the entire implant can be withdrawn. Once removed, the opening may be sealed or filled, or a new implant may be inserted.

Figure 28A:
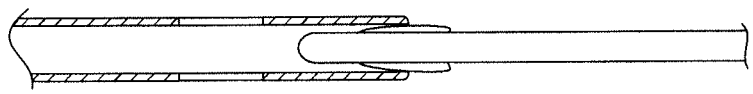
FIGS. 28A and 28B illustrate another coupling structure and method of coupling.
Figure 28B:
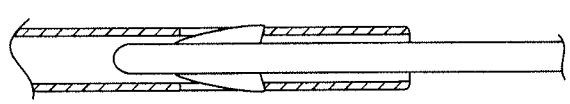

FIGS. 25-28B illustrate different coupling regions and means for coupling that may be used between the implant regions and the insertion or removal devices, or between regions of the implant. For example, in FIG. 25, the coupling region is a threaded region. FIGS. 26A and 26B illustrates a coupling region that is configured as a friction-engagement region in which the inner member is captured by an outer member and compression fit to secure the two ends together. Similarly, in FIGS. 27A and 27B the coupling means illustrated in FIGS. 26A and 26B is shown for use to expand an inner member 2701 within a surrounding outer member 2704. The inner member 2701 may include or be used with a brace, anchor or other structure that prevents it from moving (e.g., axially) during expansion. For example, a cylinder, rim, or lip (not shown) adjacent to the inner member may be used to brace the inner member during expansion. A mechanism such as this may be used to expand the plurality of arms from the implant. FIGS. 28A and 28B illustrate another variation of an engagement member in which the flanges on the inner member are compressible but allowed to expand once they reach the engagement region in the outer member and are allowed to expand, connecting the two regions.

Figure 29A:
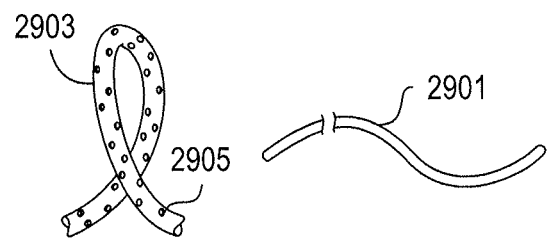
FIGS. 29A-29D show one variation of a silver-releasing arm.
Figure 29B:
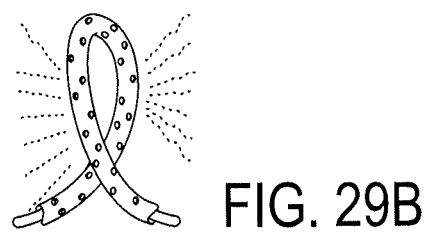
Figure 29C:
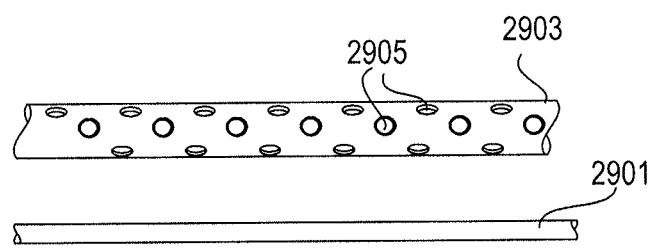
Figure 29D:
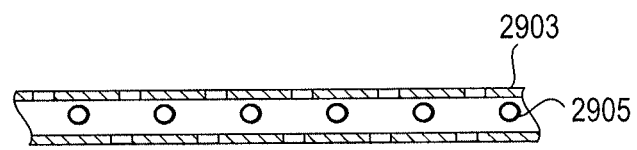

FIGS. 29A-29D illustrate one variation of a silver-releasing arm. In some variations the silver-releasing arm may be flexible, as shown in FIGS. 29A and 29B. The arm may include an inner silver depot 2901 and an outer protective cover 2903 having one or more openings 2905 from which silver may be released, as illustrated in FIG. 29B. In some variations the arms may be relatively stiff. The outer protective cover may be a metal, polymer, or the like. In some variations the arms include a shape memory material, such as a shape memory alloy, that may be pre-biased into a shape (curved, etc.). FIGS. 29C and 29D show enlarged and cross-sectional views, respectively, of a portion of the arm shown in FIGS. 29A-29B. In some variations the arm is not hollow or silver-filled, as shown in FIGS. 29A-29D, but instead is coated with silver to form the silver reservoir.

Figure 30A:
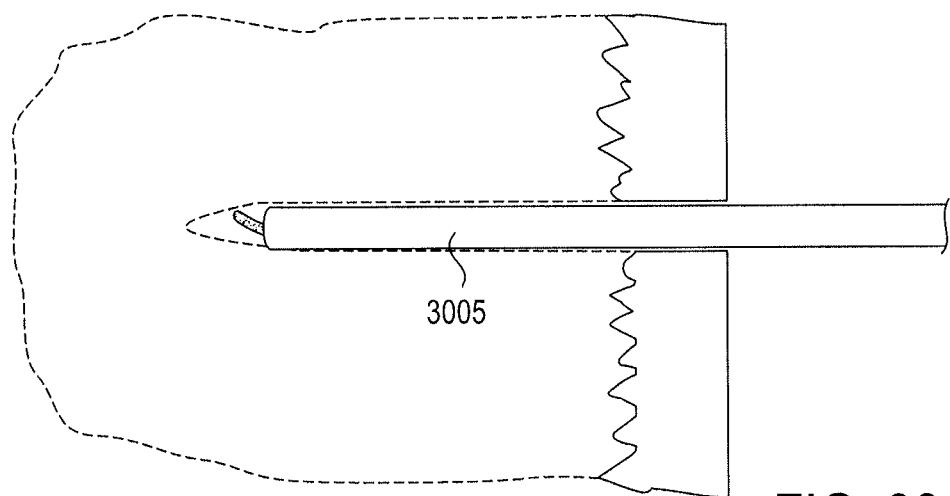
FIGS. 30A and 30B illustrate another variation of a silver-releasing implant as described herein.
Figure 30B:
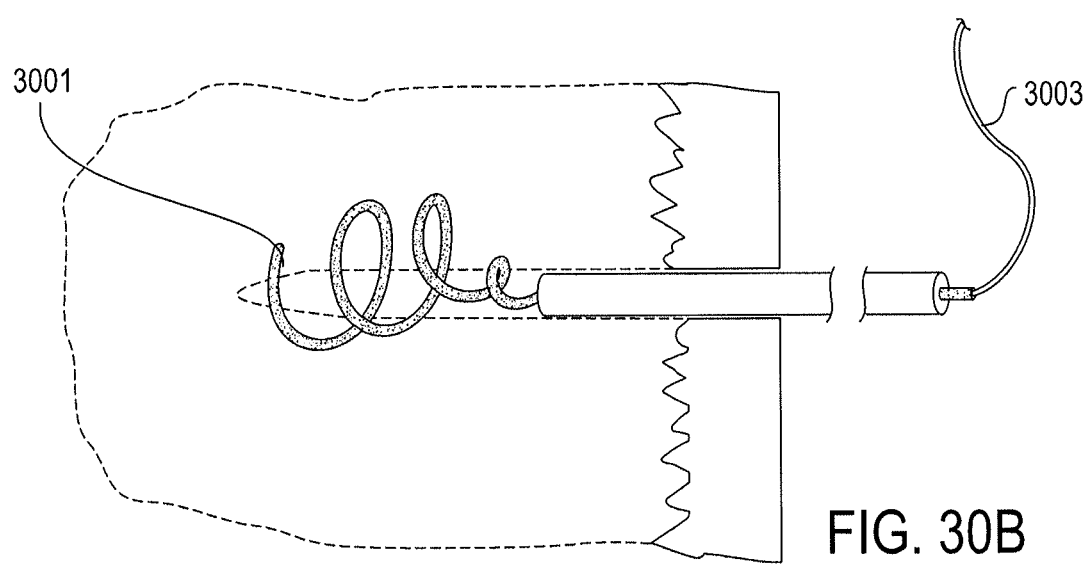

Although many of the variations described herein include a plurality of expandable arms, providing many of the advantages described above (such as reaching large bone regions), in some variations it may be desirable to use a single arm, as illustrated in FIGS. 30A and 30B. In this example, the flexible arm shown in FIGS. 29A-29D is used as an inner arm member in conjunction with an outer member (e.g., guide) for insertion in to the bone. The inner arm 3001 (including an internal silver reservoir 3003) may be extended from the outer member 3005 to drive it into the bone as illustrated in FIG. 30B. In operation, the inner member is extended from the outer member after the outer member has been inserted into the bone; the outer member is released while withdrawing it proximally, and the inner member is fed through it and into the bone.

Figure 31A:
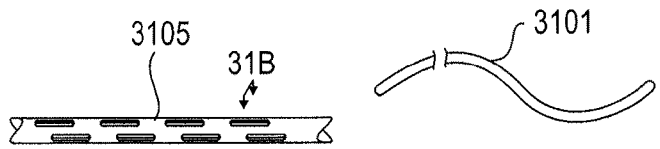
FIGS. 31A and 31B show another variation of a silver-releasing arm.
Figure 31B:
Figure 31C:
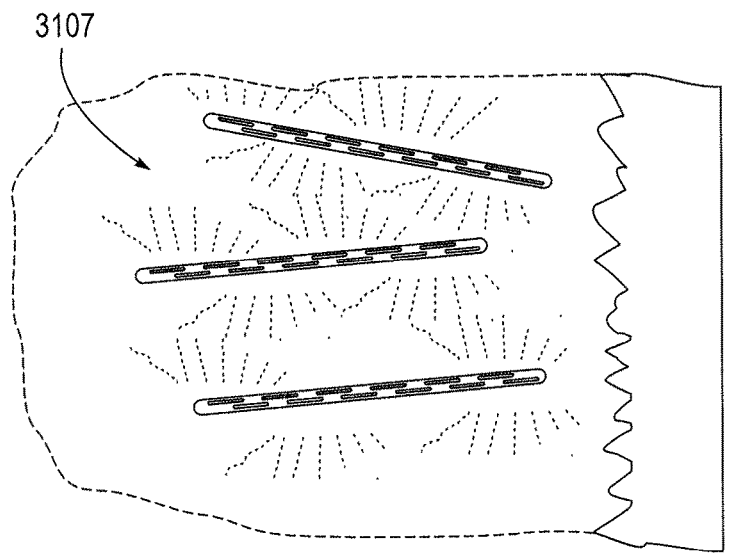
FIG. 31C illustrates another variation of silver-releasing implants deployed in a bone region.

FIGS. 31A-31C illustrate another variation of a silver-releasing arm that may be used. In this example, the arm includes an inner core of silver 3101 that is surrounded by an outer covering or scaffold 3105. In the outer covering includes openings, as seen in FIG. 31B through which the silver may be released. In any of the device variations described herein the silver released from the arms may be directly released (e.g., a silver surface may be exposed to the bone), or it may be released into a buffer or matrix through which it may move on its way into the bone.

In one variation, the implant may include just the arms, which may be inserted into the bone, as shown in FIG. 31C. In this variation each arm 3107 may include a silver release driver (such as a power source and/or a galvanic reactor metal in electrical contact with the silver reservoir).

Figure 32A:
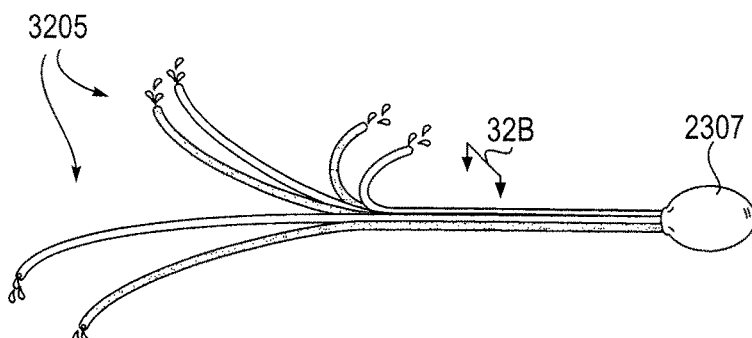
FIGS. 32A and 32B illustrate another variation of a silver-releasing implant for implantation into a bone.
Figure 32B:
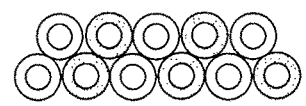

In some variations, the implant may include a liquid reservoir for delivery of a therapeutic material, which may include a solution of silver, into the bone. For example, FIG. 32A illustrates one variation of an implant having a plurality of fluid-delivery arms 3205 that are hollow and connected to a source of therapeutic fluid 2307. FIG. 32B shows a cross-section through the fluid delivery arms of the device.

Although illustrative variations of the present invention have been described above, it will be evident to one skilled in the art that various changes and modifications may be made without departing from the invention. For instance, variations of the present invention may include the release of other (including other ionic) antimicrobial, growth hormone, other drug, or the like. In addition, the present invention may include the use of the procedures described herein for therapy, repeating the procedures as often as necessary, as the amount or placement of the implant may change over time.

What is claimed is:

1. A method of preventing infection in a bone using an implantable screw having a deployed configuration in which a silver-eluting arm extends from the implantable screw and an undeployed configuration in which the arm is not extended from the implantable screw, the method comprising: inserting the implantable screw into a bone in an undeployed configuration; deploying the arm from the implantable screw into the bone, wherein deploying the arm places a silver reservoir on the arm in electrical communication with a galvanic reactor metal; galvanically releasing silver from the silver reservoir on the arm over an extended period of time at a sustained level, wherein the arm comprises a nickel titanium alloy covered by an adhesion layer and a silver coating, wherein the adhesion layer is formed after removal of a titanium oxide layer from the outer surface of the nickel titanium alloy and before the silver coating.

2. The method of claim 1, wherein inserting comprises inserting the implantable screw in the undeployed configuration in which the silver reservoir is not in electrical communication with the galvanic reactor metal.

3. The method of claim 1, wherein deploying comprises extending the arm from a passageway through the implantable screw and out of a distal region of the implantable screw.

4. The method of claim 1, wherein deploying comprises placing the silver reservoir in direct contact with the galvanic reactor metal.

5. The method of claim 1, wherein inserting the implantable screw comprises inserting the implantable screw into a patient's foot.

6. The method of claim 1, wherein inserting the implantable screw comprises inserting the implantable screw into a patient with diabetes and/or poor blood circulation.

7. The method of claim 1, further comprising removing the arm from the implantable screw and replacing the arm with a new arm after the period of time.

* * * * *